United States Patent
Jang et al.

(10) Patent No.: US 10,461,259 B2
(45) Date of Patent: Oct. 29, 2019

(54) ORGANIC LIGHT EMITTING DEVICE

(71) Applicant: LG CHEM, LTD., Seoul (KR)

(72) Inventors: Boon Jae Jang, Daejeon (KR); Dong Hoon Lee, Daejeon (KR); Jung Oh Huh, Daejeon (KR); Min Young Kang, Daejeon (KR); Dong Uk Heo, Daejeon (KR); Mi Yeon Han, Daejeon (KR); Min Woo Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/767,296

(22) PCT Filed: Oct. 18, 2017

(86) PCT No.: PCT/KR2017/011537
§ 371 (c)(1),
(2) Date: Apr. 10, 2018

(87) PCT Pub. No.: WO2018/074845
PCT Pub. Date: Apr. 26, 2018

(65) Prior Publication Data
US 2019/0067591 A1    Feb. 28, 2019

(51) Int. Cl.
*H01L 51/00*    (2006.01)
*H01L 51/50*    (2006.01)
*H01L 51/52*    (2006.01)
*C07D 251/24*   (2006.01)
*C07D 403/10*   (2006.01)

(52) U.S. Cl.
CPC ........ *H01L 51/0067* (2013.01); *C07D 251/24* (2013.01); *C07D 403/10* (2013.01); *H01L 51/00* (2013.01); *H01L 51/0052* (2013.01); *H01L 51/0054* (2013.01); *H01L 51/0056* (2013.01); *H01L 51/0058* (2013.01); *H01L 51/0072* (2013.01); *H01L 51/52* (2013.01); *H01L 51/5004* (2013.01); *H01L 51/508* (2013.01); *H01L 51/5008* (2013.01); *H01L 51/5012* (2013.01); *H01L 51/5016* (2013.01); *H01L 51/5056* (2013.01)

(58) Field of Classification Search
None
See application file for complete search history.

(56) References Cited

U.S. PATENT DOCUMENTS

| | | | |
|---|---|---|---|
| 6,225,467 B1 | 5/2001 | Esteghamatian et al. | |
| 9,502,669 B2 | 11/2016 | Huh et al. | |
| 9,960,363 B2 * | 5/2018 | Eum | C07D 239/26 |
| 2004/0018383 A1 | 1/2004 | Aziz et al. | |
| 2007/0176167 A1 * | 8/2007 | Parthasarathy | H01L 51/56 257/40 |
| 2014/0077179 A1 | 3/2014 | Shin et al. | |
| 2015/0162543 A1 | 6/2015 | Lee et al. | |
| 2015/0380662 A1 | 12/2015 | Kim et al. | |

(Continued)

FOREIGN PATENT DOCUMENTS

| | | |
|---|---|---|
| CN | 103189469 A | 7/2013 |
| CN | 103298800 A | 9/2013 |

(Continued)

*Primary Examiner* — Thien F Tran
(74) *Attorney, Agent, or Firm* — Dentons US LLP

(57) ABSTRACT

The present invention provides an organic light emitting device having improved driving voltage, efficiency and lifetime.

12 Claims, 1 Drawing Sheet

(56) References Cited

U.S. PATENT DOCUMENTS

| | | |
|---|---|---|
| 2016/0111664 A1 | 4/2016 | Ito et al. |
| 2016/0126471 A1 | 5/2016 | Lui et al. |
| 2016/0181524 A1 | 6/2016 | Lee et al. |
| 2016/0322583 A1 | 11/2016 | Kim et al. |
| 2018/0013072 A1 | 1/2018 | Eum et al. |
| 2018/0053900 A1 | 2/2018 | Eum et al. |

FOREIGN PATENT DOCUMENTS

| | | |
|---|---|---|
| CN | 104356137 A | 2/2015 |
| CN | 104835921 A | 8/2015 |
| EP | 3016169 A1 | 5/2016 |
| EP | 3 127 988 A1 | 2/2017 |
| JP | 2004063465 A | 2/2004 |
| JP | 2012-204793 A | 10/2012 |
| JP | 2018506847 A | 3/2018 |
| JP | 2018507174 A | 3/2018 |
| KR | 10-2000-0051826 A | 8/2000 |
| KR | 10-2014-0009919 A | 1/2014 |
| KR | 10-2015-0077284 A | 7/2015 |
| KR | 10-2015-0115688 A | 10/2015 |
| KR | 10-2016-0019846 A | 2/2016 |
| KR | 10-2016-0039492 A | 4/2016 |
| KR | 10-2016-0046076 A | 4/2016 |
| KR | 10-2016-0050894 A | 5/2016 |
| KR | 10-2016-0060569 A | 5/2016 |
| KR | 10-2016-0076010 A | 6/2016 |
| KR | 10-2016-0078237 A | 7/2016 |
| TW | 201615629 A | 5/2016 |

\* cited by examiner

[FIG. 1]
[FIG. 2]
[FIG. 3]
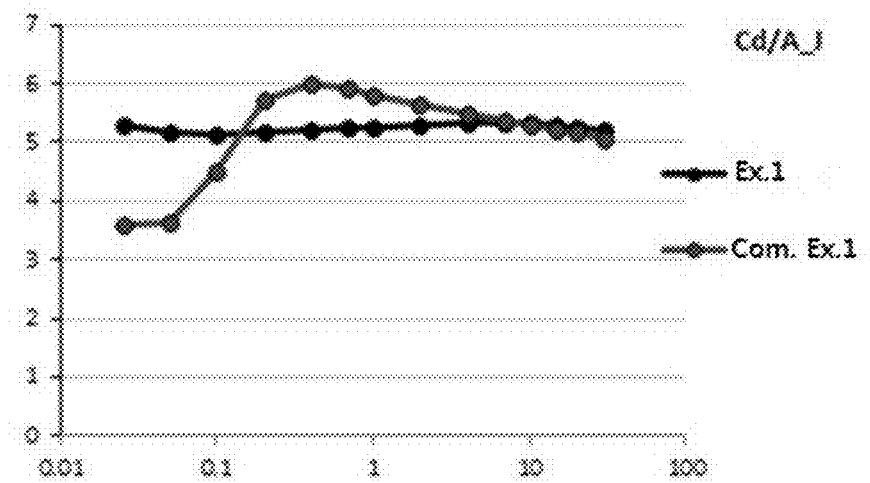

ORGANIC LIGHT EMITTING DEVICE

CROSS-REFERENCE TO RELATED APPLICATION(S)

This application is a National Stage Application of International Application No. PCT/KR2017/011537 filed Oct. 18, 2017, and claims the benefit of Korean Patent Application No. 10-2016-0135296 filed Oct. 18, 2016, all of which are hereby incorporated by reference in their entirety for all purposes as if fully set forth herein.

The present invention relates to an organic light emitting device having improved driving voltage, efficiency and lifetime.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing demand for developing an organic light emitting device having improved driving voltage, efficiency and lifetime.

PRIOR ART LITERATURE

Patent Literature (Patent Literature 1) Korean Patent Laid-open Publication No. 10-2000-0051826

DETAILED DESCRIPTION OF THE INVENTION

Technical Problem

It is one object of the present invention to provide an organic light emitting device having improved driving voltage, efficiency and lifetime.

Technical Solution

The present invention provides an organic light emitting device comprising:

a first electrode;
a hole transport layer;
a light emitting layer;
a power efficiency enhancement layer;
a gradation enhancement layer; and
a second electrode,
wherein the power efficiency enhancement layer comprises a compound represented by Chemical Formula 1 below, and
the gradation enhancement layer comprises a compound represented by Chemical Formula 2 below:

[Chemical Formula 1]

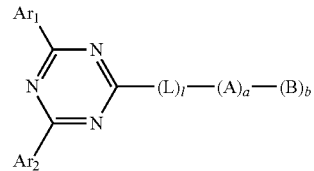

in Chemical Formula 1,
$Ar_1$ and $Ar_2$ are each independently a substituted or unsubstituted $C_{6-60}$ aryl; or a substituted or unsubstituted $C_{2-60}$ heteroaryl containing at least one of O, N, Si and S,
each L is independently a direct bond, or a substituted or unsubstituted $C_{6-60}$ arylene,
each A is independently a substituted or unsubstituted $C_{6-60}$ arylene having a meta- or ortho-linking group,
each B is independently a substituted or unsubstituted $C_{6-60}$ aryl; or a substituted or unsubstituted $C_{2-60}$ heteroaryl containing at least one of O, N, Si and S,
l is an integer of 0 to 2,
a is an integer of 1 or 2, and
b is an integer of 1 or 2,

[Chemical Formula 2]

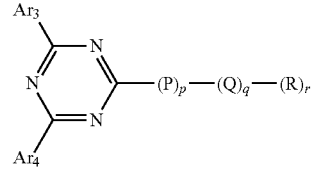

in Chemical Formula 2,
$Ar_3$ and $Ar_4$ are each independently a substituted or unsubstituted $C_{6-60}$ aryl; or a substituted or unsubstituted $C_{2-60}$ heteroaryl containing at least one of O, N, Si and S,
each P is independently a direct bond, or a substituted or unsubstituted $C_{6-60}$ arylene,
each Q is independently a substituted or unsubstituted $C_{6-60}$ arylene having a para-linking group,
each R is independently a substituted or unsubstituted $C_{6-60}$ aryl; or a substituted or unsubstituted $C_{2-60}$ heteroaryl containing at least one of O, N, Si and S,
p is an integer of 0 to 2,
q is an integer of 1 or 2, and
r is an integer of 1 or 2.

Advantageous Effects

The organic light emitting device described above is excellent in driving voltage, efficiency, and lifetime.

BRIEF DESCRIPTION OF DRAWINGS

FIG. 1 shows an example of an organic light emitting device comprising a substrate 1, an anode 2, a hole transport layer 3, a light emitting layer 4, a power efficiency enhancement layer 5, a gradation enhancement layer 6, and a cathode 7.

FIG. 2 shows an example of an organic light emitting device comprising a substrate 1, an anode 2, a hole transport layer 3, a light emitting layer 4, a power efficiency enhancement layer 5, a gradation enhancement layer 6, an electron injection layer 8 and a cathode 7.

FIG. 3 is a graph showing a change in the efficiency caused by electric current applied to the organic light-emitting element of Example 1 of the present invention and Comparative Example 1.

DETAILED DESCRIPTION OF THE EMBODIMENTS

Hereinafter, the present invention will be described in more detail to help understanding of the present invention.

In the present specification,

means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be compounds having the following structures, but is not limited thereto.

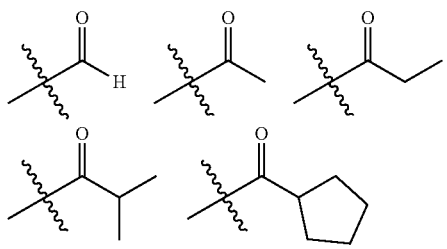

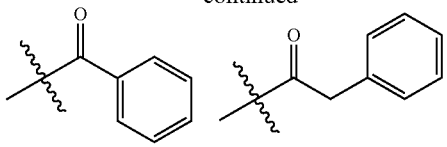

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

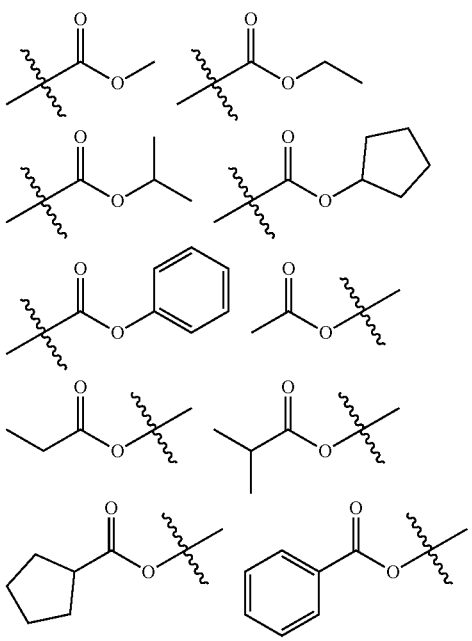

In the present specification, the number of carbon atoms in an imide group is not particularly limited, but is preferably 1 to 25. Specifically, the imide group may be compounds having the following structures, but is not limited thereto.

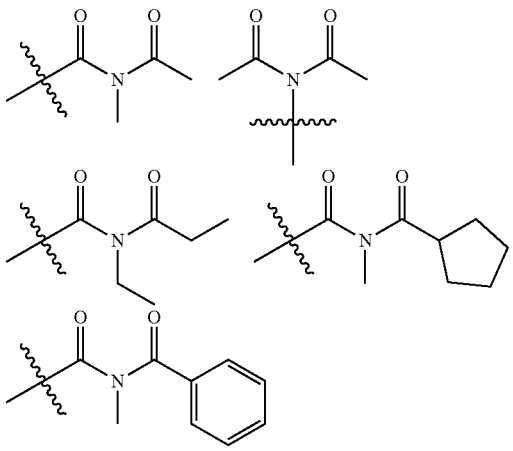

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group or the like, but is not limited thereto.

In the present specification, a fluorenyl group may be substituted, and two substituent groups may be linked with each other to form a spiro structure. In the case where the fluorenyl group is substituted,

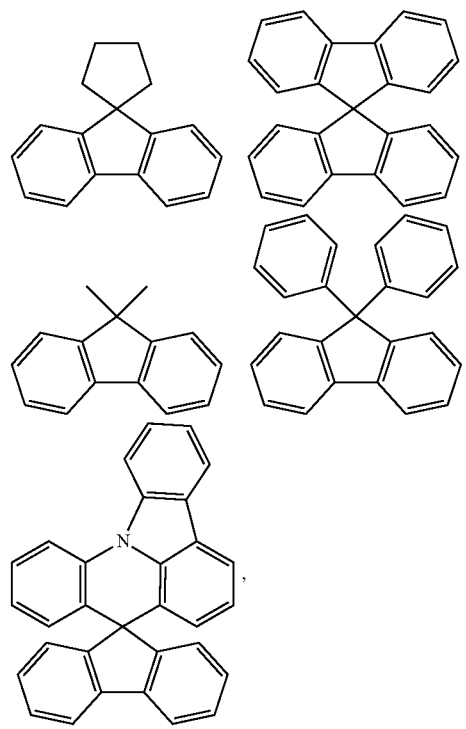

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

The present invention provides an organic light emitting device comprising: a first electrode; a hole transport layer; a light emitting layer; a power efficiency enhancement layer; a gradation enhancement layer; and a second electrode, wherein the power efficiency enhancement layer comprises a compound represented by Chemical Formula 1, and wherein the gradation enhancement layer comprises a compound represented by Chemical Formula 2 is provided.

The organic light emitting device according to the present invention comprises a power efficiency enhancement layer and a gradation enhancement layer, and thus can improve the driving voltage, efficiency and lifetime of the organic light emitting device.

Hereinafter, the present invention will be described in detail for each configuration.

First Electrode and Second Electrode

The first electrode and the second electrode used in the present invention are electrodes used in an organic light emitting device. For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

In addition, a hole injection layer may be further included on the anode. The hole injection layer is composed of a hole injection material, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability.

It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

Hole Transport Layer

The hole transport layer used in the present invention is a layer that can receive the holes from the anode or the hole injection layer formed on the anode and transport the holes to the light emitting layer. The hole transport material is suitably a material having large mobility to the holes, which may receive holes from the anode or the hole injection layer and transfer the holes to the light emitting layer.

Specific examples thereof include an arylamine-based organic material, a conductive polymer, a block copolymer in which a conjugate portion and a non-conjugate portion are present together, and the like, but are not limited thereto.

Light Emitting Layer

The light emitting material contained in the light emitting layer is a material that can receive the holes and the electrons from the hole transport layer and the electron transport layer, respectively, and bond the holes and the electrons to emit light in a visible ray region, and is preferably a material having good quantum efficiency to fluorescence or phosphorescence.

Specific examples thereof comprise a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic cycle derivative, a heterocycle-containing compound, or the like. Specific examples of the condensation aromatic cycle derivative include an anthracene derivative, a pyrene derivative, a naphthalene derivative, a pentacene derivative, a phenanthrene compound, a fluoranthene compound, and the like, and examples of the heterocycle-containing compound include a carbazole derivative, a dibenzofuran derivative, a ladder-type furan compound, a pyrimidine derivative, and the like, but are not limited thereto.

Particularly, as the host of the light emitting layer, a compound represented by Chemical Formula 3 below is preferred.

[Chemical Formula 3]

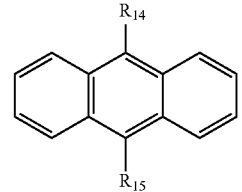

in Chemical Formula 3, $R_{14}$ and $R_{15}$ are each independently a substituted or unsubstituted $C_{6-60}$ aryl.

Representative examples of the compound represented by Chemical Formula 3 are as follows:

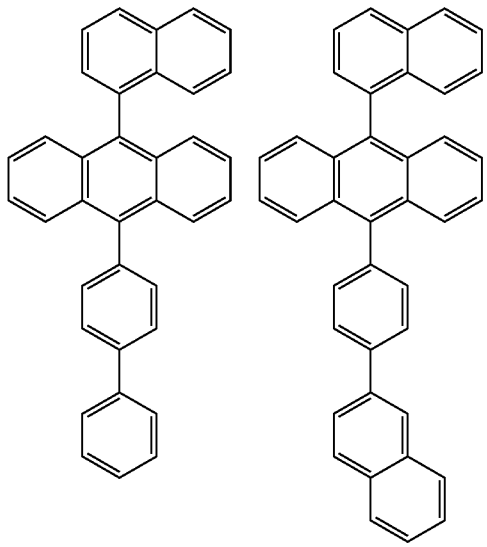

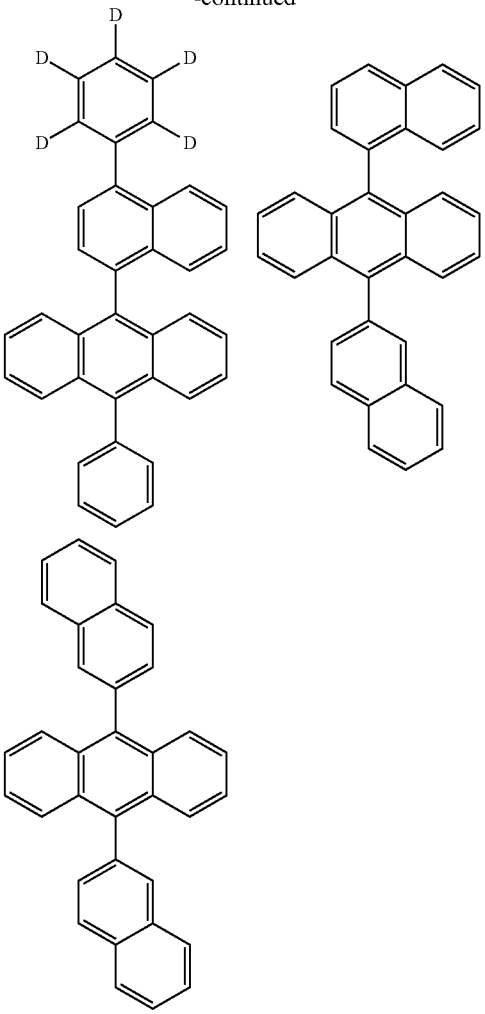

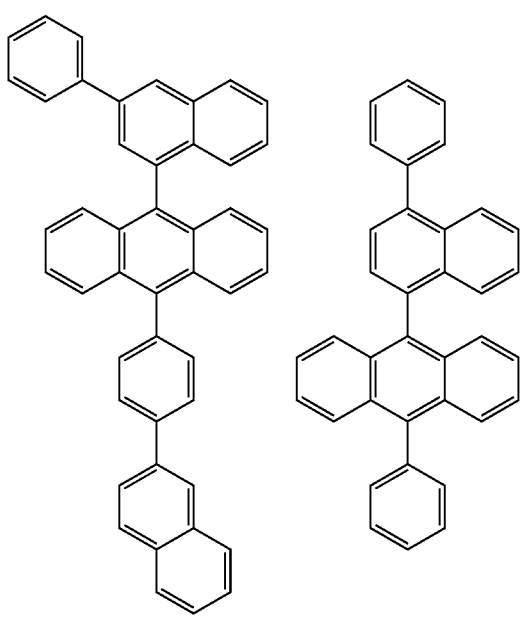

Examples of the dopant material include an aromatic amine derivative, a styrylamine compound, a boron complex, a fluoranthene compound, a metal complex, and the like. Specifically, the aromatic amine derivative is a condensation aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

Power Efficiency Enhancement Layer

The power efficiency enhancement layer means a layer which is formed on the light emitting layer and thus serves to improve the mobility of electrons and thus enhance the power efficiency of the organic light emitting device. Particularly, in the present invention, the compound represented by Chemical Formula 1 is used as the material of the power efficiency enhancement layer.

Preferably, each A is independently selected from the group consisting of the following:
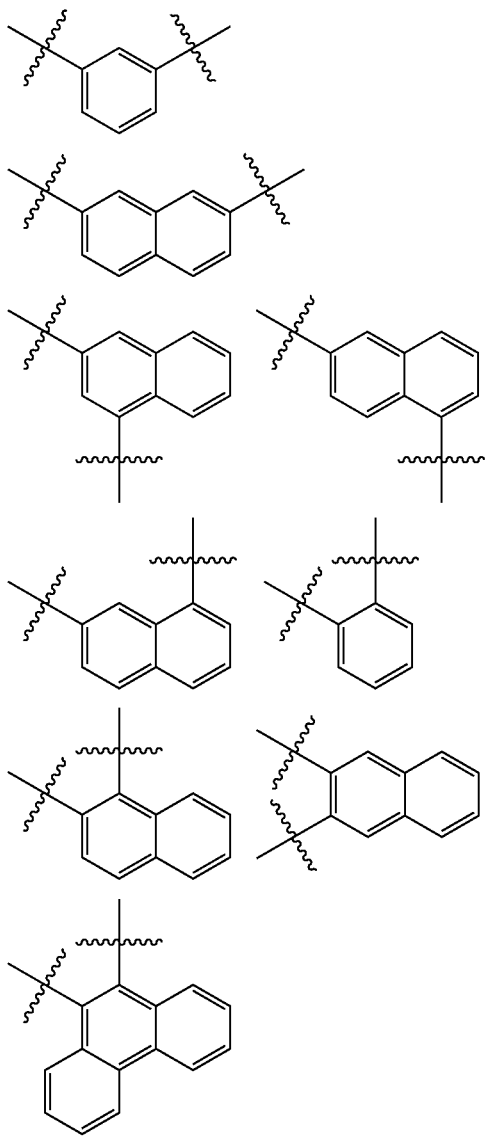
Preferably, Ar$_1$ and Ar$_2$ are each independently phenyl, biphenylyl, or naphthyl.
Preferably, L is a single bond, or phenylene.
Preferably, B is any one selected from the group consisting of the following:
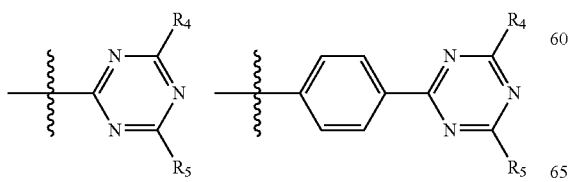
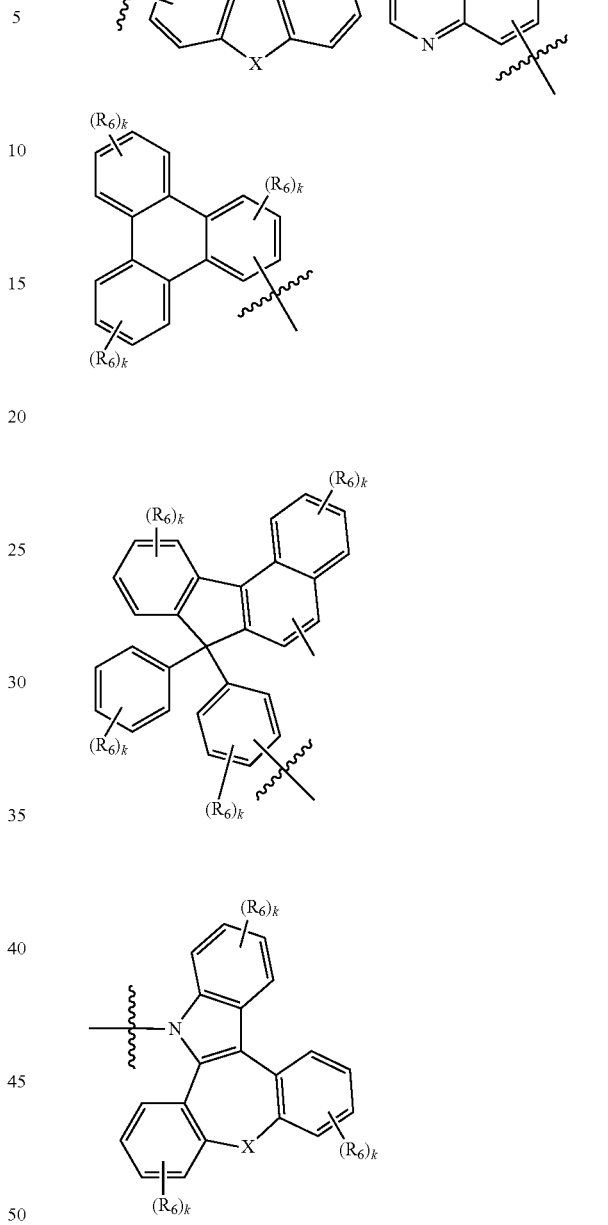
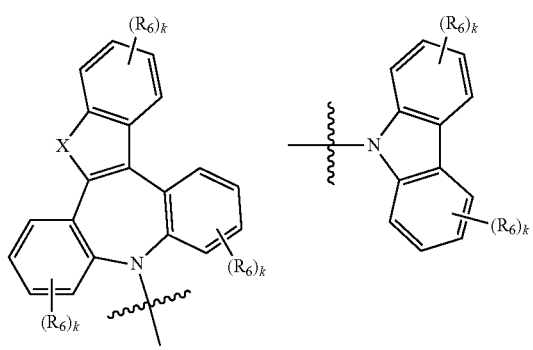

-continued

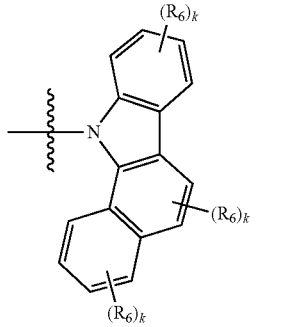

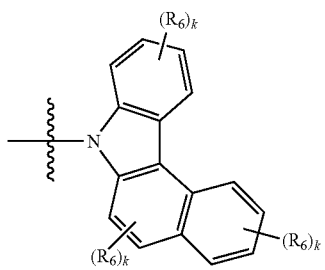

-continued

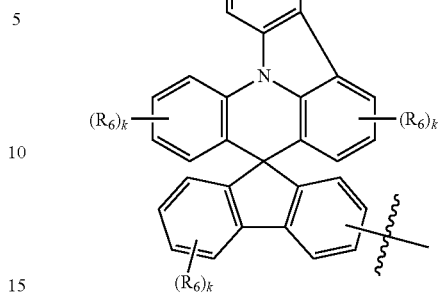

wherein, $R_4$ to $R_6$ are each independently hydrogen; deuterium; halogen; cyano; nitro; amino; a substituted or unsubstituted $C_{1-60}$ alkyl; a $C_{1-60}$ haloalkyl; a substituted or unsubstituted $C_{1-60}$ haloalkoxy; a substituted or unsubstituted $C_{3-60}$ cycloalkyl; a substituted or unsubstituted $C_{2-60}$ alkenyl group; a substituted or unsubstituted $C_{6-60}$ aryl; or a substituted or unsubstituted $C_{6-60}$ heteroaryl containing at least one of O, N, Si and S, X is $CR_7R_8$, $NR_7$, S, or O, $R_7$ and $R_8$ are each independently a $C_{1-60}$ alkyl, or a $C_{6-60}$ aryl, or $R_7$ and $R_8$ together form a $C_{6-60}$ aromatic ring when X is $CR_7R_8$, and k is an integer of 0 to 2.

Preferably, l, a and b are 1.

Representative examples of the compound represented by Chemical Formula 1 are as follows:

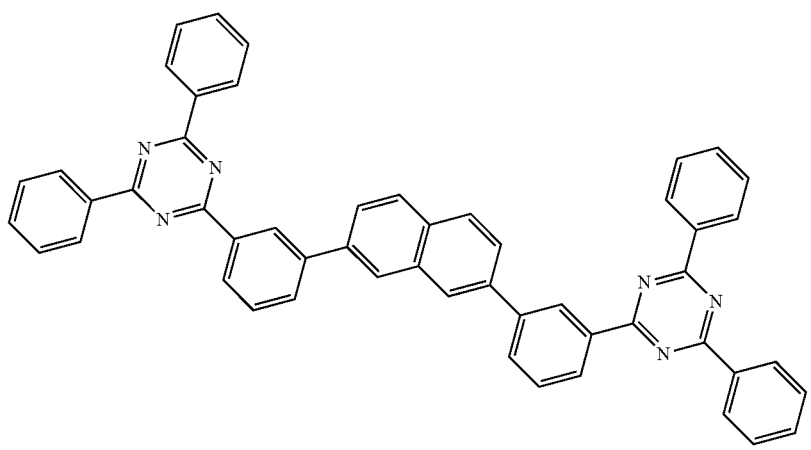

-continued
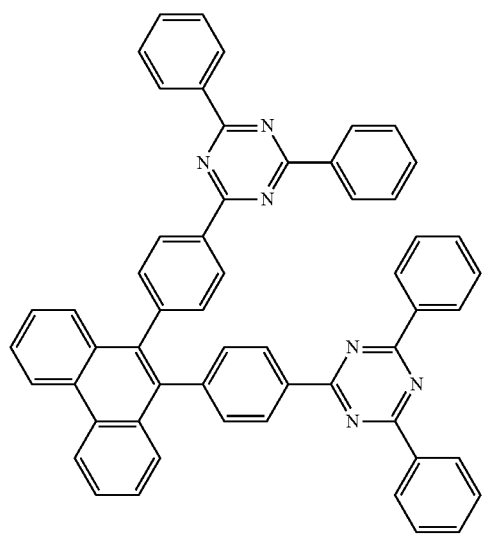
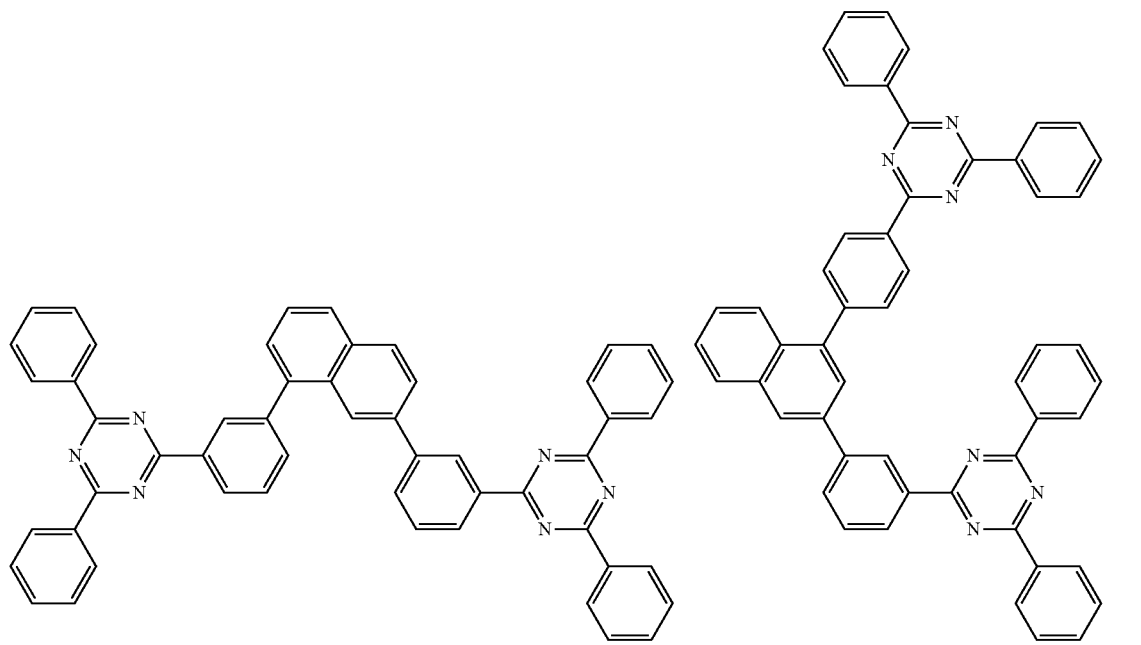
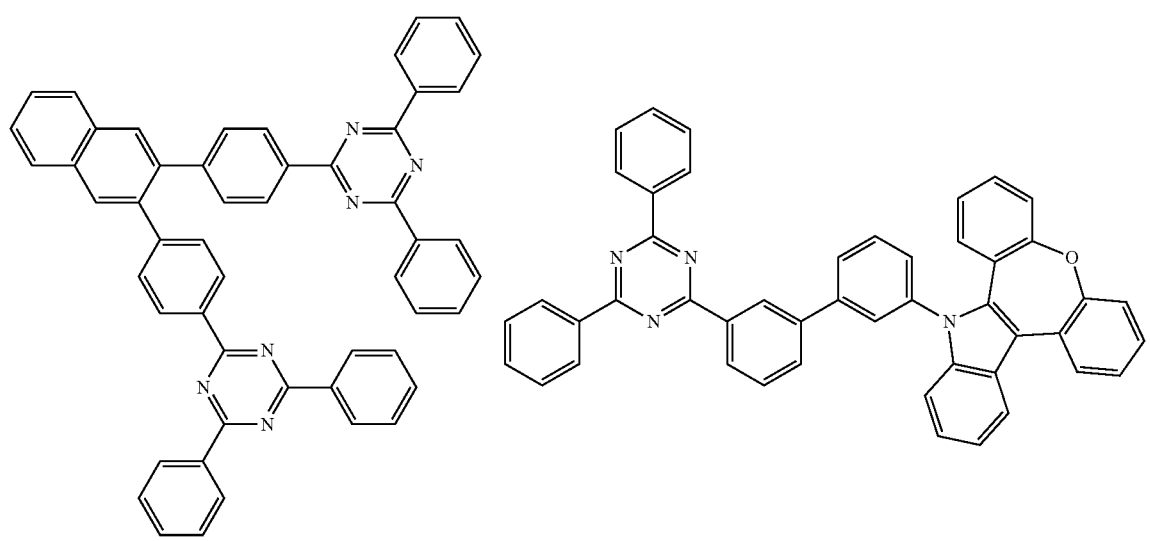

-continued
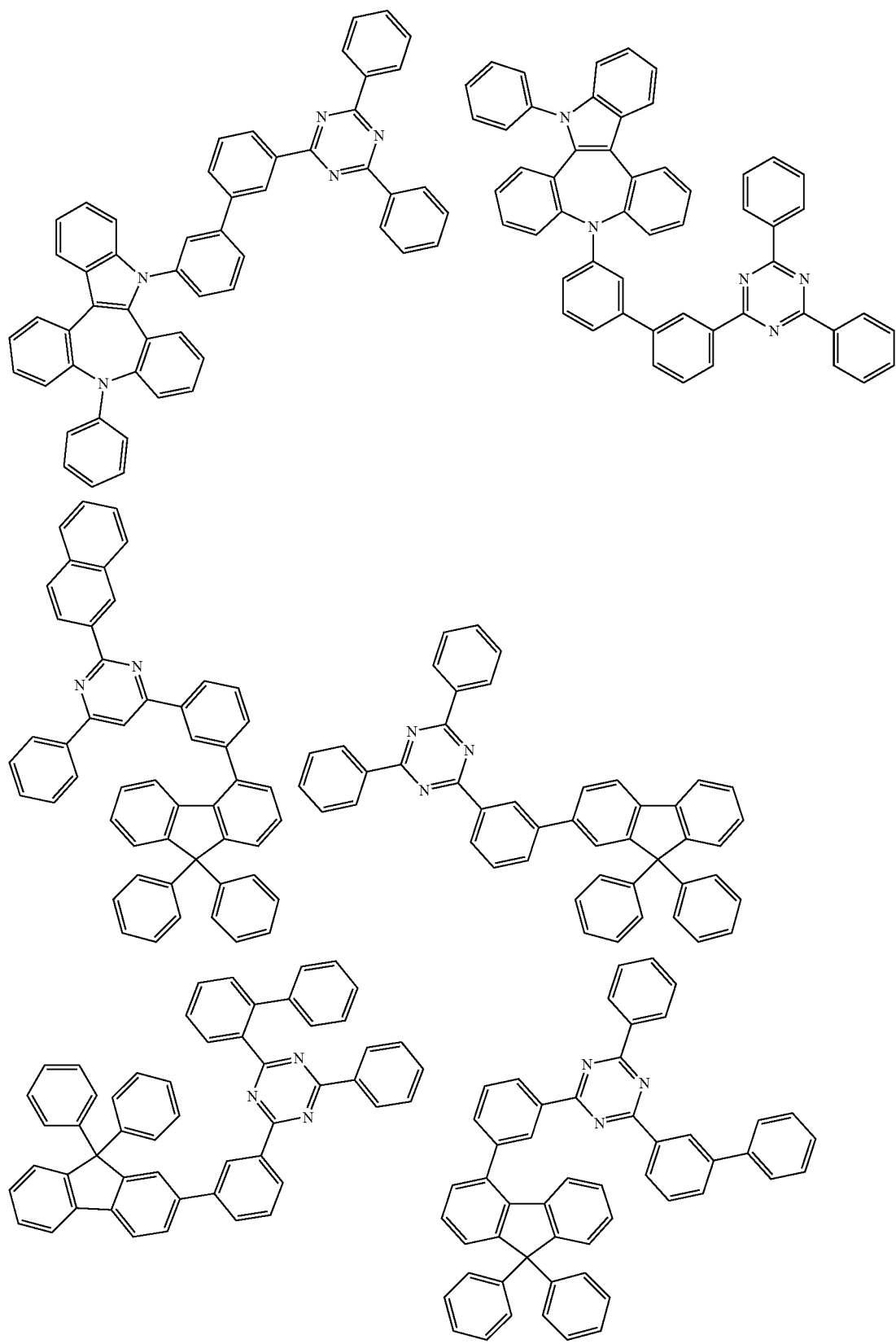

-continued
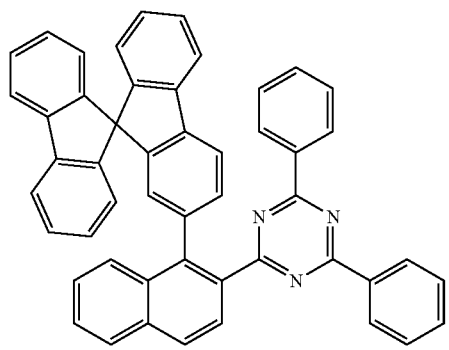
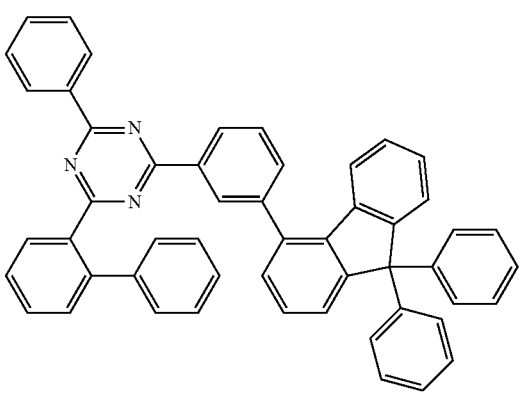
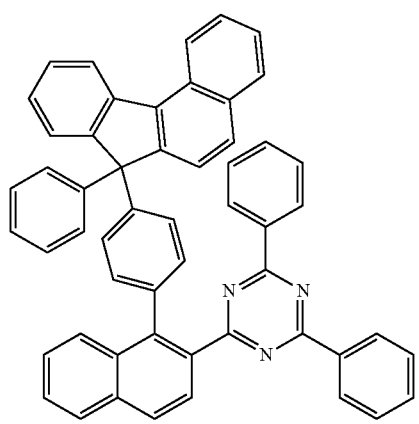
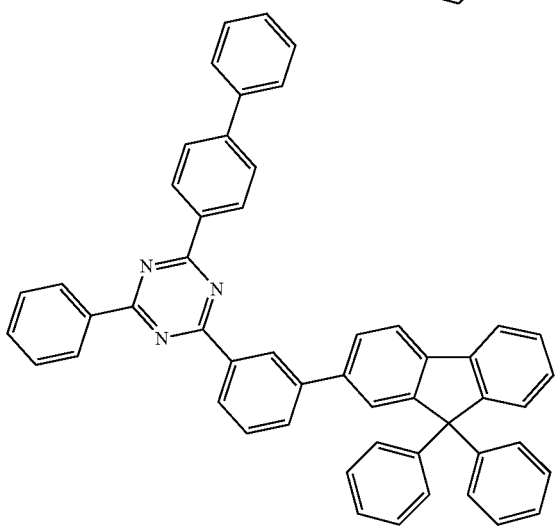
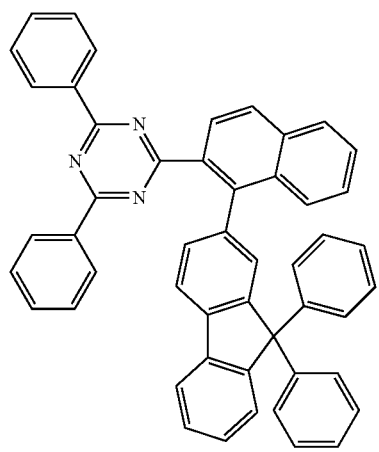
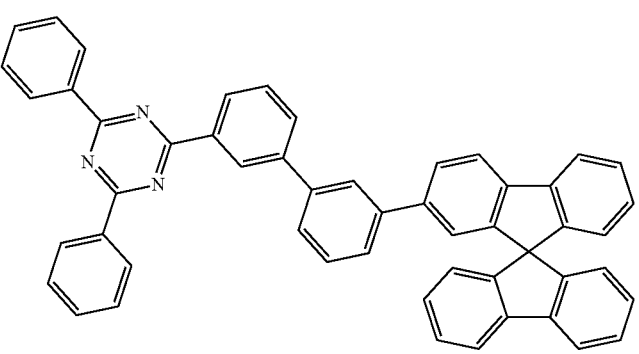
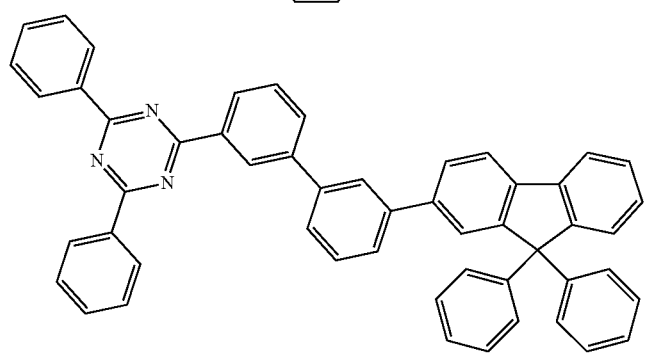

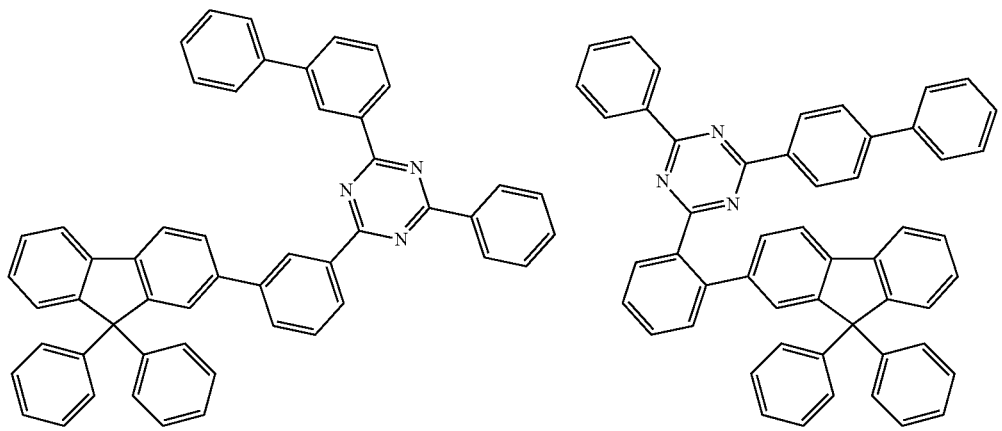
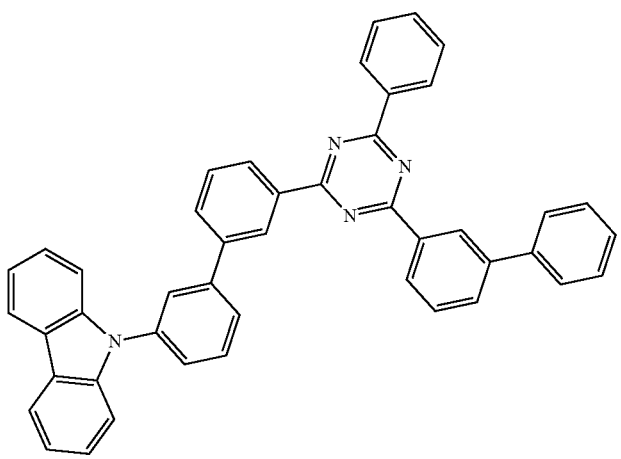
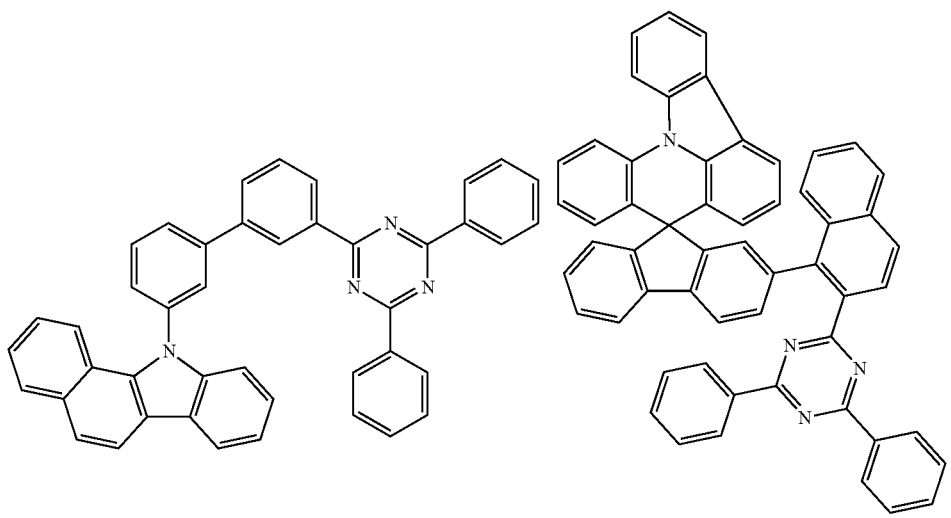

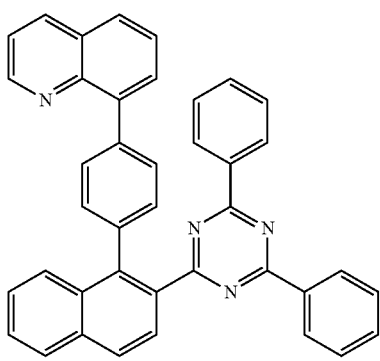
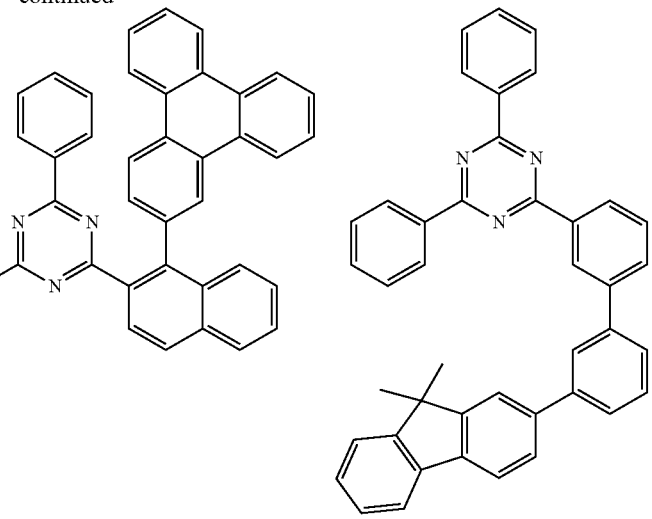
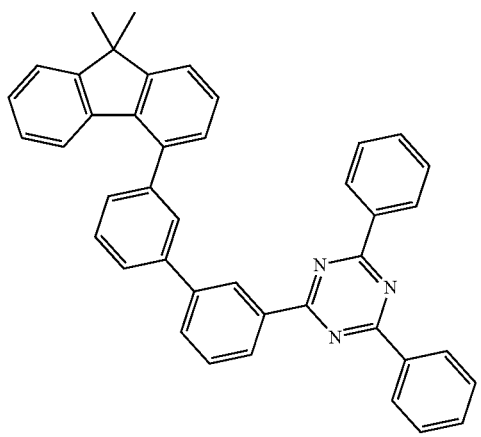
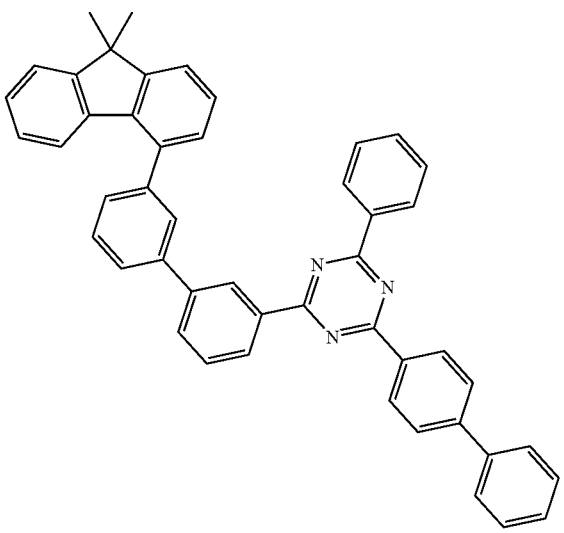

In addition, the triplet energy of the compound represented by Chemical Formula 1 is preferably 2.2 eV or more.

Further, the present invention provides, for example, a method for preparing a compound represented by Chemical Formula 1 as shown in Reaction Scheme 1 below.

[Reaction Scheme 1]

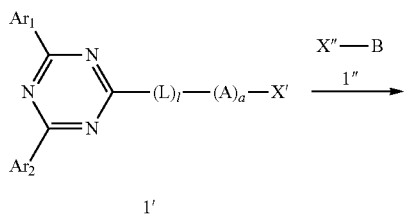

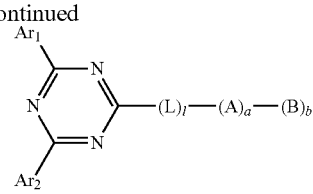

Reaction Scheme 1 is a Suzuki coupling reaction in which a compound represented by Chemical Formula 1' and a compound represented by Chemical Formulas 1" are reacted to produce a compound represented by Chemical Formula 1. The X' is halogen (preferably, bromo or chloro) and the X" is $B(OH)_2$. The production method can be further specified in the preparation examples described later.

In addition, the compound represented by Chemical Formula 1 has a higher electron mobility than the compound represented by Chemical Formula 2 used in the gradation enhancement layer as described later.

Gradation Enhancement Layer

The gradation enhancement layer means a layer which is formed on the power efficiency enhancement layer and thus serves to improve the mobility of electrons and enhances the power efficiency of the organic light emitting device. Particularly, in the present invention, the compound represented by Chemical Formula 2 is used as the material of the gradation enhancement layer.

Preferably, each Q is independently selected from the group consisting of the following:

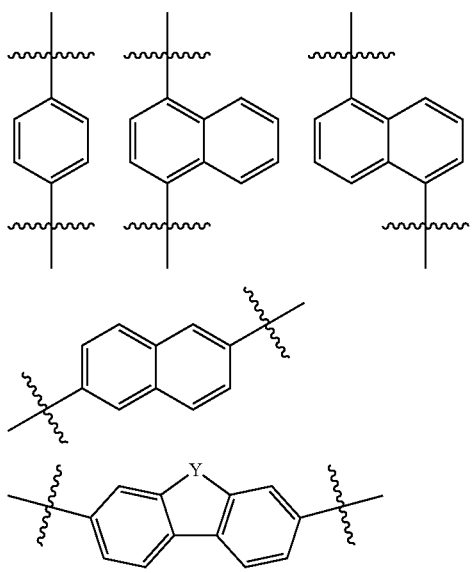

wherein,

Y is $CR'_1R'_2$, S, or O, $R'_1$ and $R'_2$ are each independently a $C_{1-60}$ alkyl, or $C_{6-60}$ aryl, or $R'_1$ and $R'_2$ together form a $C_{6-60}$ aromatic ring.

Preferably, P is a single bond, or phenylene.

Preferably, R is any one selected from the group consisting of the following:

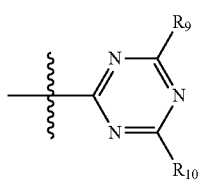

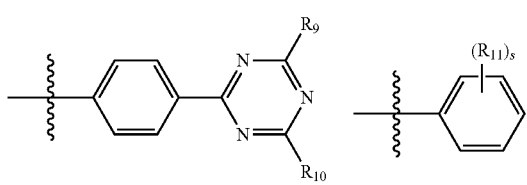

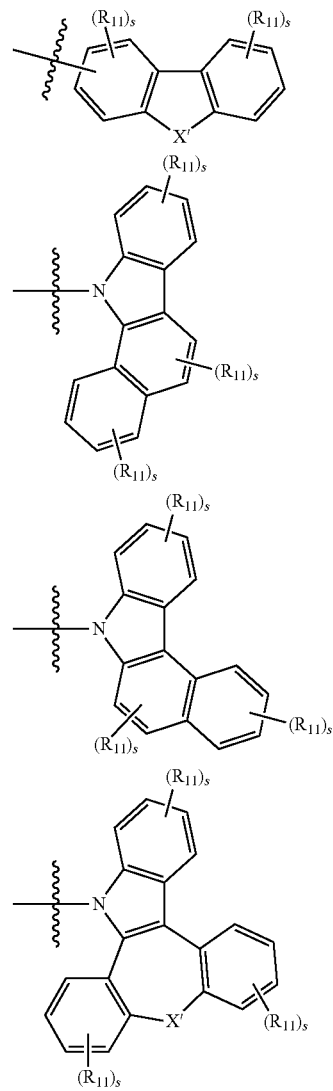

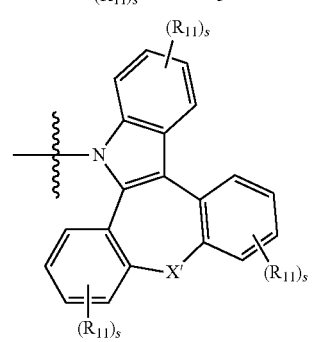

wherein, $R_9$ to $R_{11}$ are each independently hydrogen; deuterium; halogen; cyano; nitro; amino; a substituted or unsubstituted $C_{1-60}$ alkyl; a $C_{1-60}$ haloalkyl; a substituted or unsubstituted $C_{1-60}$ haloalkoxy; a substituted or unsubstituted $C_{3-60}$ cycloalkyl; a substituted or unsubstituted $C_{2-60}$ alkenyl group; a substituted or unsubstituted $C_{6-60}$ aryl; or a substituted or unsubstituted $C_{6-60}$ heteroaryl containing at least one of O, N, Si and S, X' is $CR_{12}R_{13}$, $NR_{12}$, S, or O, $R_{12}$ and $R_{13}$ are each independently a $C_{1-60}$ alkyl, or a $C_{6-60}$ aryl, or $R_{12}$ and $R_{13}$ together form a $C_{6-60}$ aromatic ring when X' is $CR_{12}R_{13}$, and s is an integer of 0 to 2.

Preferably, p, q and r are 1.

Representative examples of the compound represented by Chemical Formula 2 are as follows:

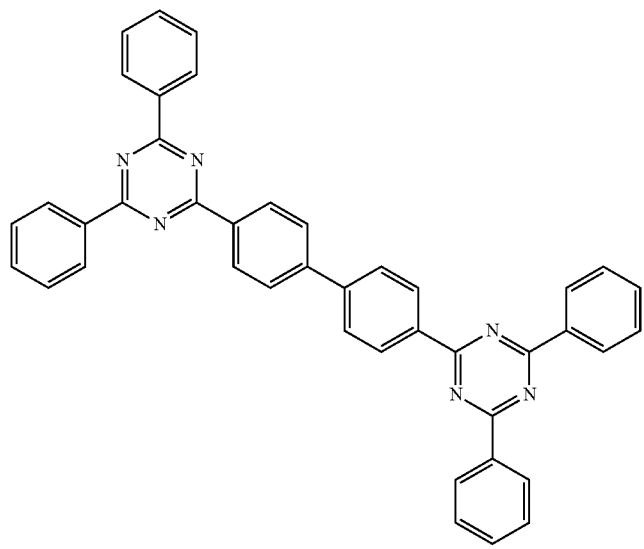
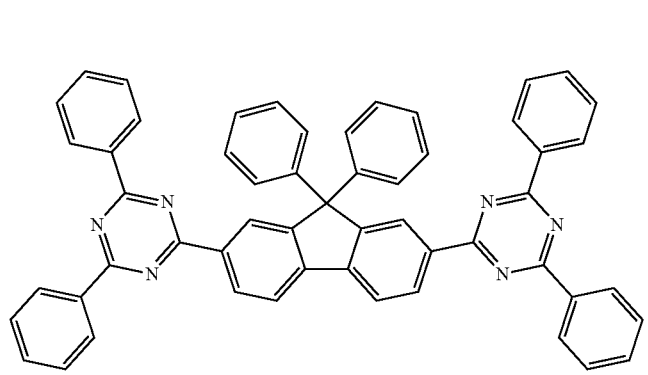
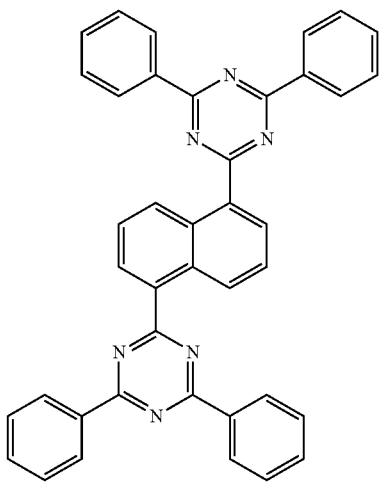
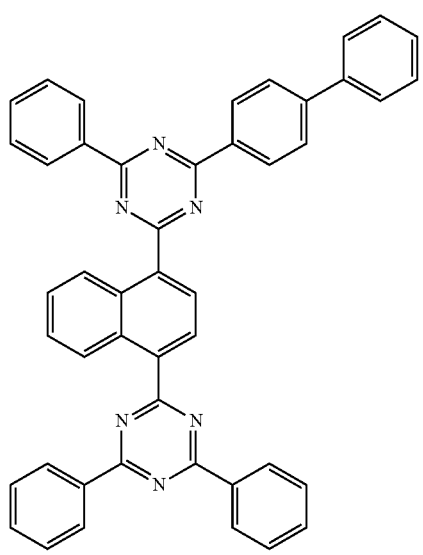
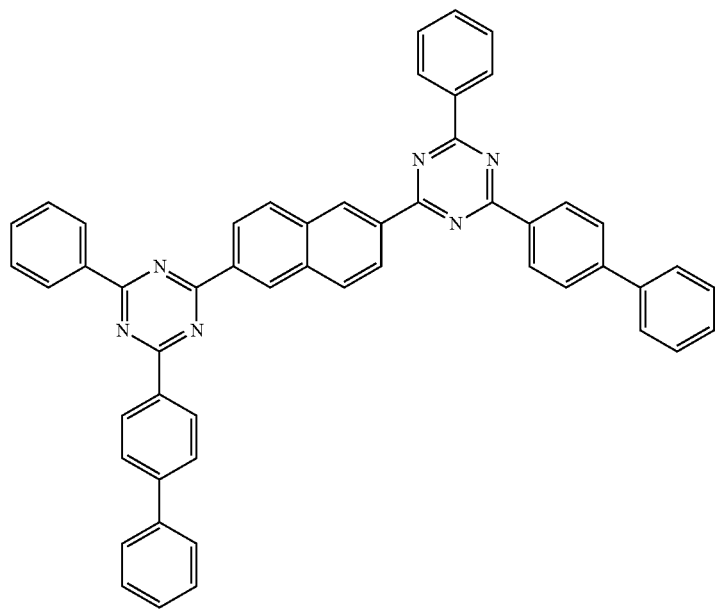

-continued
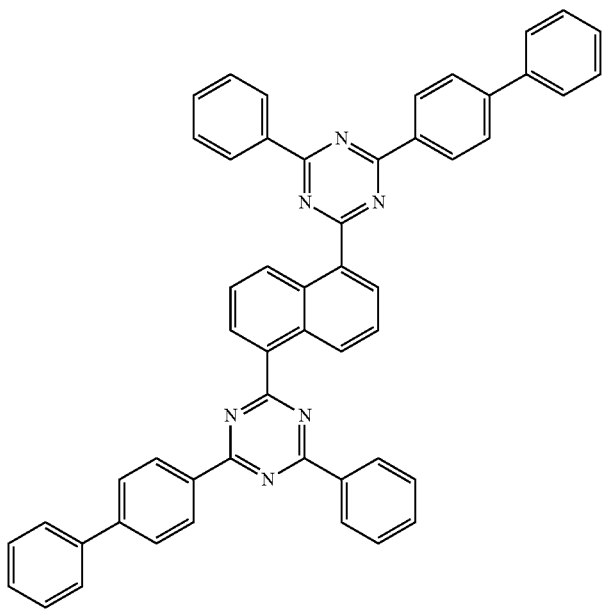
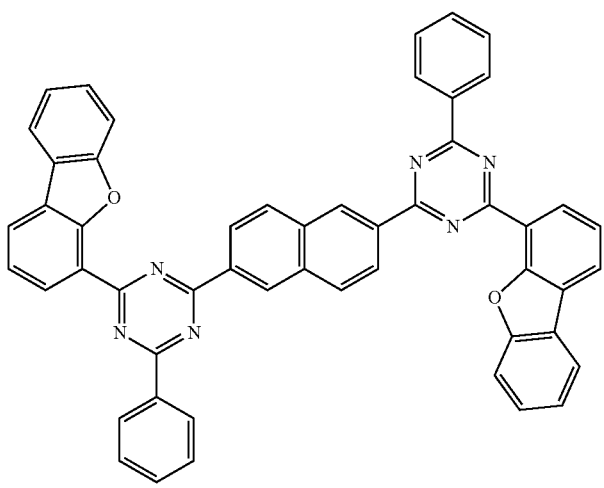
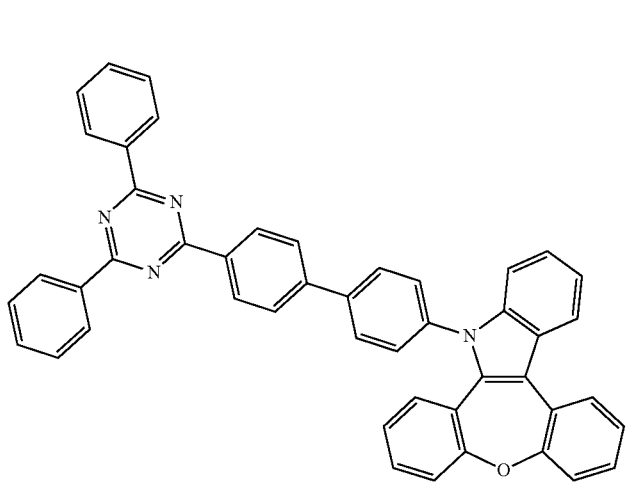
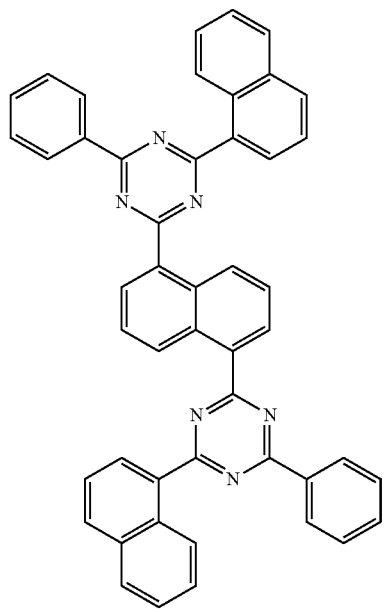

-continued
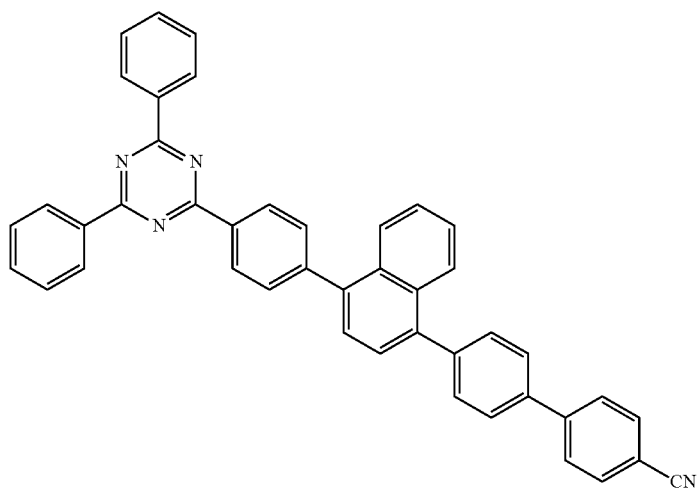
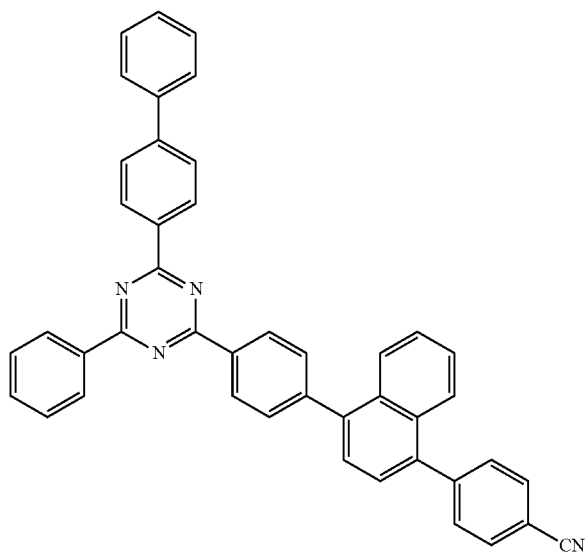
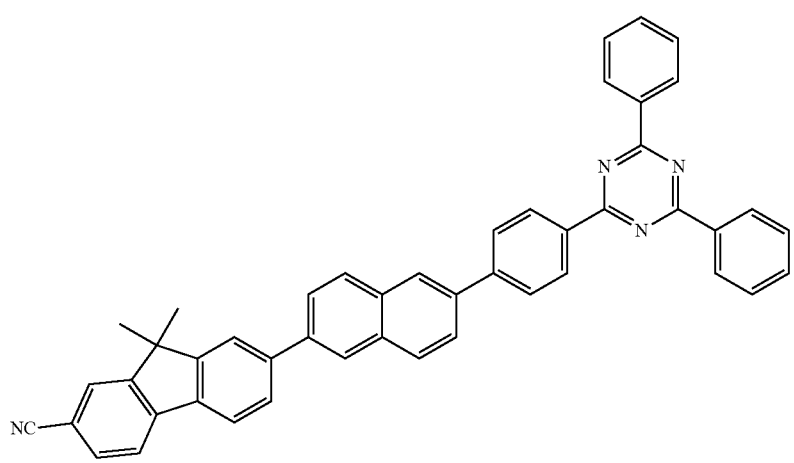

-continued
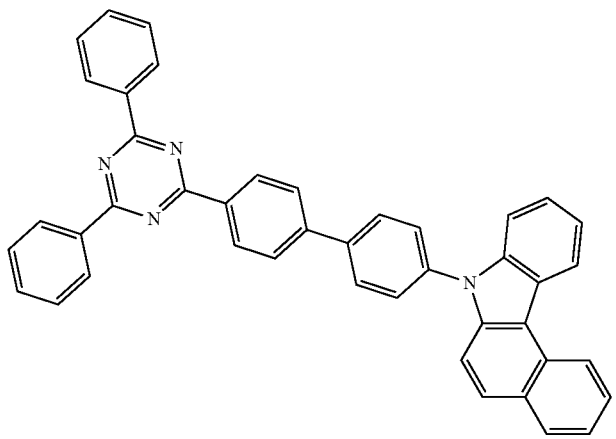
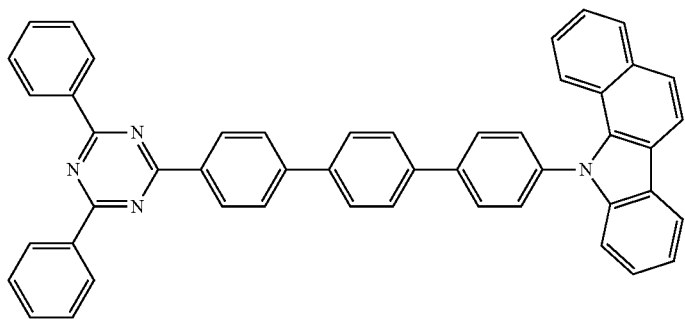
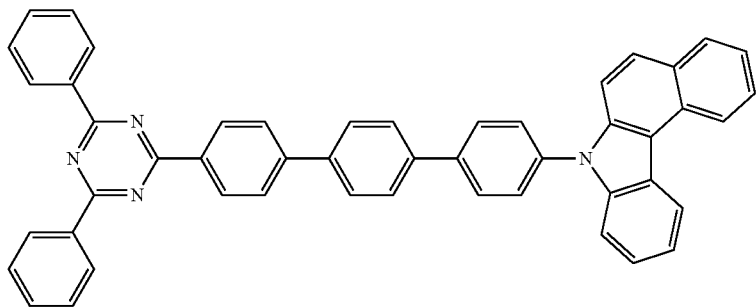
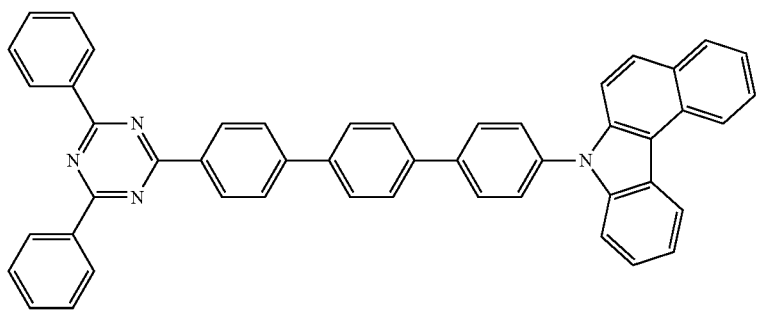

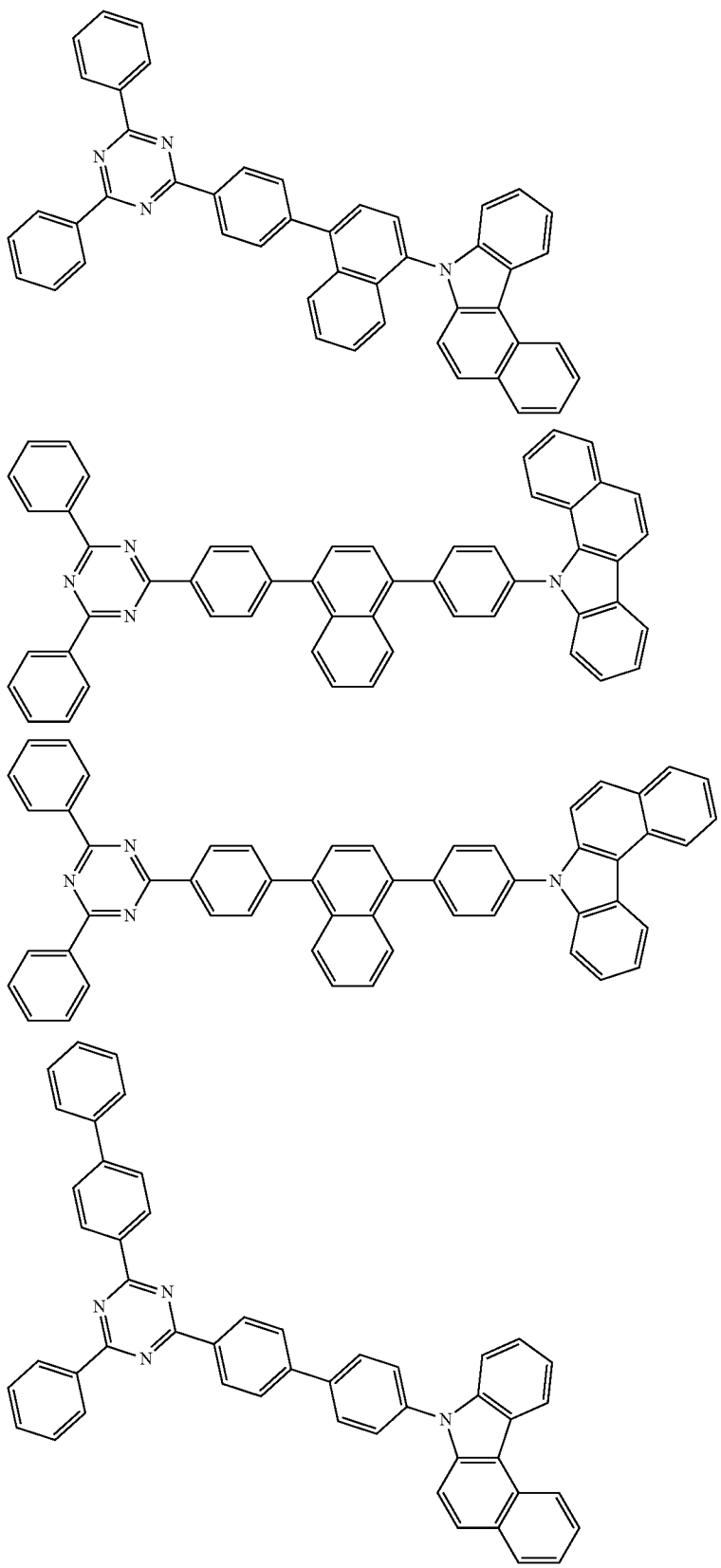

-continued

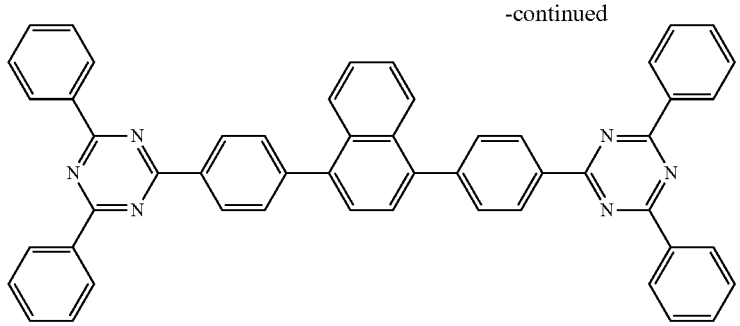

The triplet energy of the compound represented by Chemical Formula 2 is preferably 2.2 eV or more.

In addition, the present invention provides, for example, a method for preparing a compound represented by Chemical Formula 2 as shown in Reaction Scheme 2 below.

[Reaction Scheme 2]

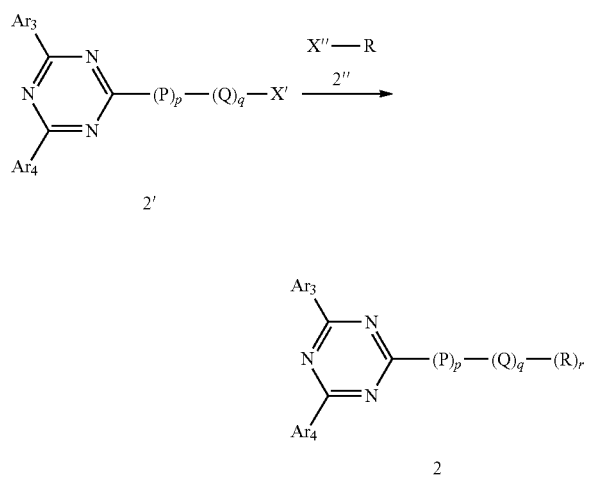

Reaction Scheme 2 is a Suzuki coupling reaction in which a compound represented by Chemical Formula 2' and a compound represented by Chemical Formulas 2" are reacted to produce a compound represented by Chemical Formula 2. The X' is halogen (preferably, bromo or chloro) and the X" is B(OH)$_2$. The production method can be further specified in the preparation example described later.

Moreover, the gradation enhancement layer may further include an electron transport material. The electron transport material is a material that can receive the electrons well from the cathode and transport the electrons to the light emitting layer, and a material having large mobility to the electrons is suitable. Specific examples thereof include an 8-hydroxyquinoline Al complex; a complex including Alq$_3$; an organic radical compound; a hydroxyflavone-metal complex, and the like, but are not limited thereto.

Further, the gradation enhancement layer may further include an n-type dopant. In this case, the n-type dopant may be included in an amount of 20 to 80% by weight of the gradation enhancement layer. The n-type dopant is not limited as long as it is used for an organic light emitting device. For example, a compound represented by Chemical Formula 4 below may be used:

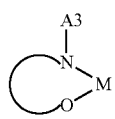

[Chemical Formula 4]

in Chemical Formula 4,

A3 is hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; or a substituted or unsubstituted heterocyclic group, the curve represents the bonds and 2 or 3 atoms required to form a 5- or 6-membered ring with M, the atoms being substituted or unsubstituted with one or more substituent groups identical to the definition of A, and M is an alkali metal or an alkaline earth metal.

Preferably, the compound represented by Chemical Formula 4 is represented by Chemical Formulas 4-1 or 4-2 below:

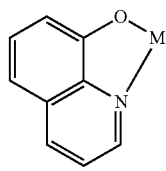

[Chemical Formula 4-1]

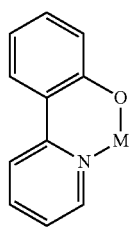

[Chemical Formula 4-2]

in Chemical Formulas 4-1 and 4-2,

M is the same as defined in Chemical Formula 4,

Chemical Formulas 4-1 and 4-2 are each independently substituted or unsubstituted by one or two or more substituent groups selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group, or adjacent substituent groups are linked with each other to form a substituted or unsubstituted hydrocarbon ring or a substituted or unsubstituted heterocyclic ring.

Preferably, the compound represented by Chemical Formula 4 is any one selected from the group consisting of the following:

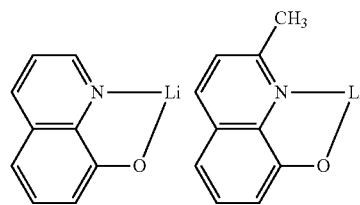

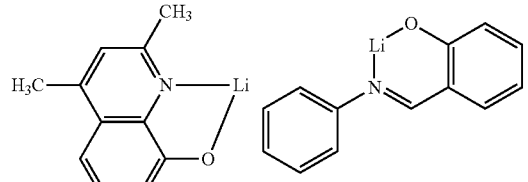

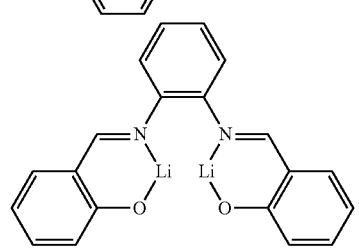

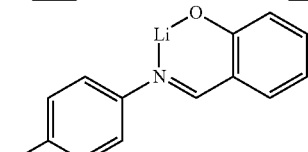

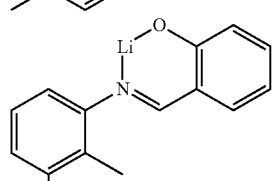

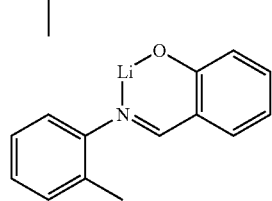

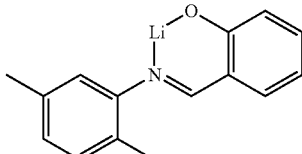

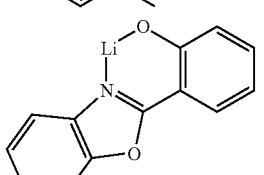
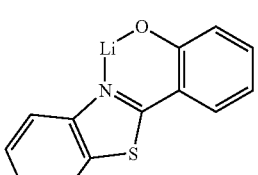

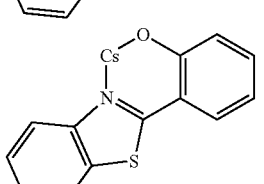

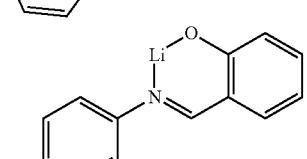

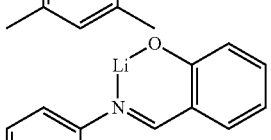

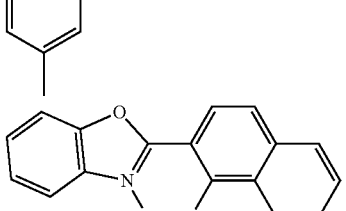

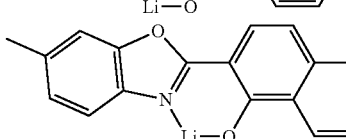

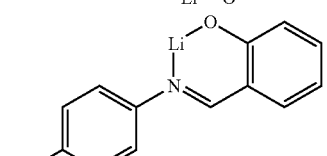

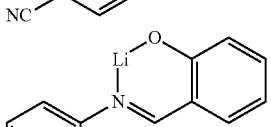

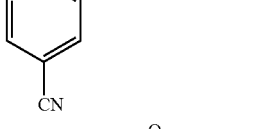

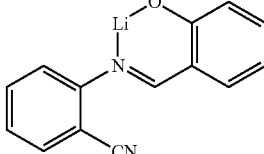

-continued
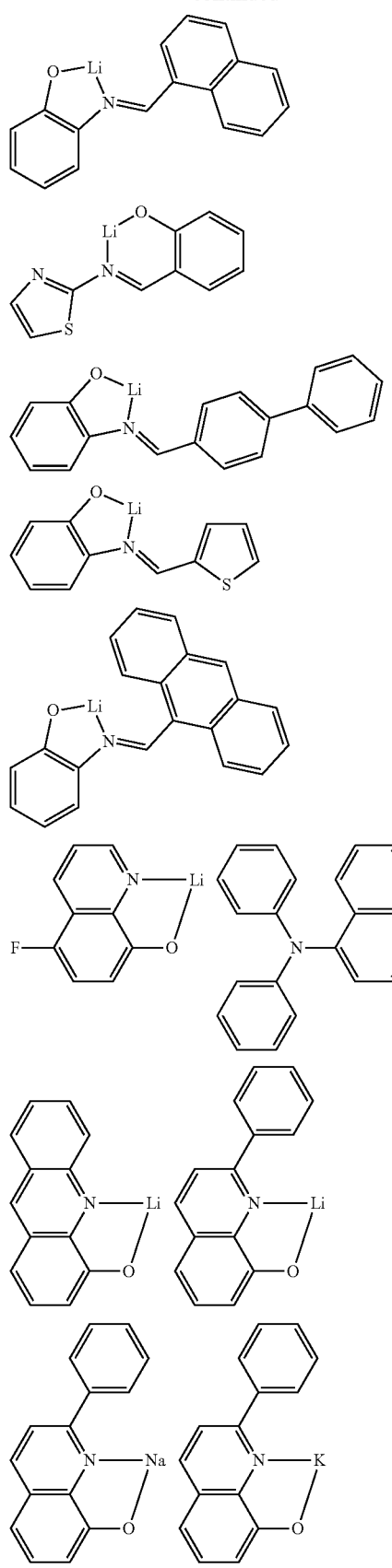
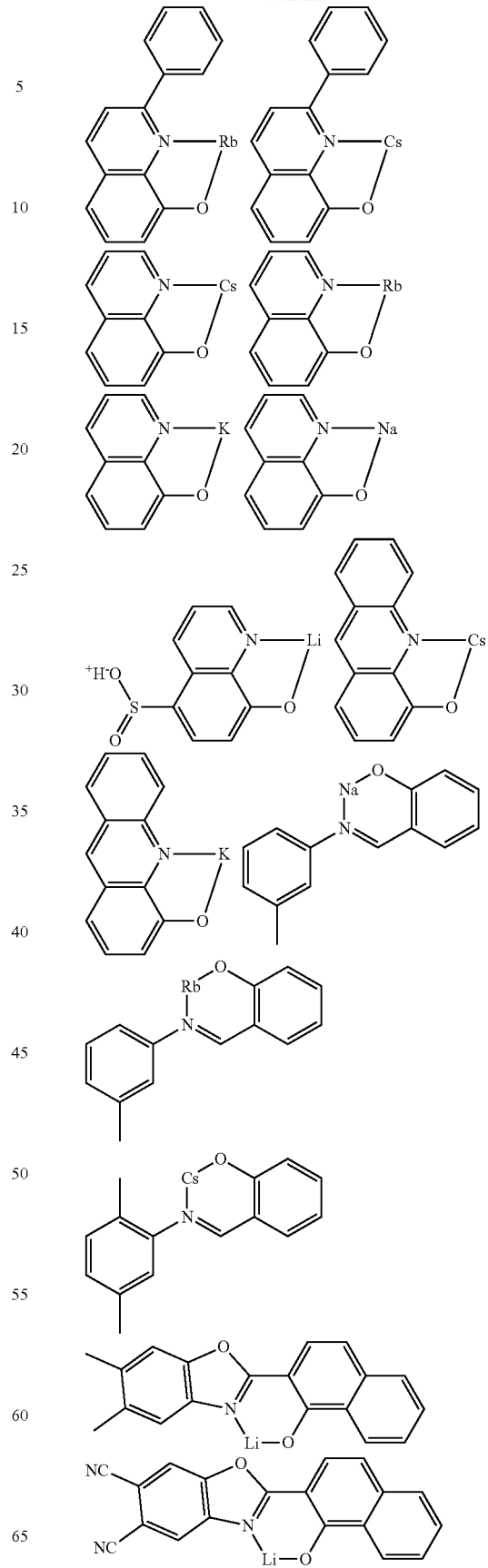

-continued

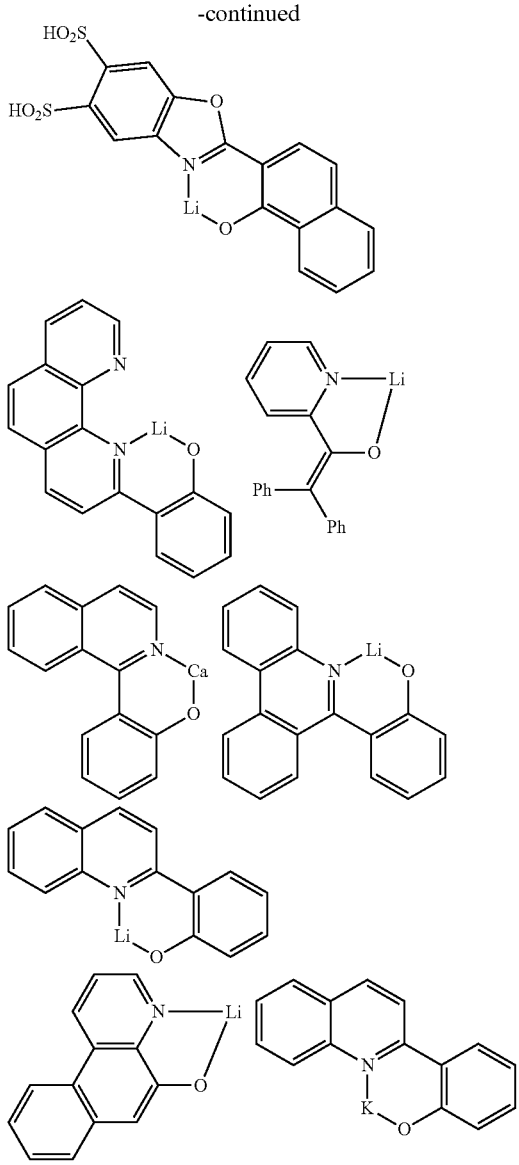

The above structures may be substituted or unsubstituted by one or two or more substituent groups selected from the group consisting of hydrogen; deuterium; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted aryl group; and a substituted or unsubstituted heterocyclic group.

Electron Injection Layer

The organic light emitting device according to the present invention may further include an electron injection layer between the gradation enhancement layer and the cathode. The electron injection layer is a layer injecting the electrons from the electrode, and a compound which has an ability of transporting the electrons, an electron injection effect from the cathode, and an excellent electron injection effect to the light emitting layer or the light emitting material, and prevents movement of an exciton generated in the light emitting layer to the hole injection layer, and has an excellent thin film forming ability is preferable.

Specific examples of materials that can be used as the electron injection layer include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

Organic Light Emitting Device

The structure of the organic light emitting device according to the present invention is illustrated in FIGS. 1 and 2. FIG. 1 shows an example of an organic light emitting device comprising a substrate 1, an anode 2, a hole transport layer 3, a light emitting layer 4, a power efficiency enhancement layer 5, a gradation enhancement layer 6, and a cathode 7. FIG. 2 shows an example of an organic light emitting device comprising a substrate 1, an anode 2, a hole transport layer 3, a light emitting layer 4, a power efficiency enhancement layer 5, a gradation enhancement layer 6, an electron injection layer 8 and a cathode 7.

The organic light emitting device according to the present invention may be manufactured by sequentially laminating the above-described configuration. In this case, the organic light emitting device may be manufactured by depositing a metal, metal oxides having conductivity, or an alloy thereof on the substrate by using a PVD (physical vapor deposition) method such as a sputtering method or an e-beam evaporation method to form an anode, forming the above-described respective layers thereon, and then depositing a material that can be used as a cathode thereon. In addition to such a method, the organic light emitting device may be manufactured by sequentially depositing a cathode material, an organic material layer, and an anode material on the substrate. Further, the light emitting layer may be formed by subjecting the host and the dopant to a vacuum deposition method as well as a solution coating method. Herein, the solution coating method means spin coating, dip coating, doctor blading, inkjet printing, screen printing, spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

On the other hand, the organic light emitting device according to the present invention may be a front side light emission type, a back side light emission type, or a double side light emission type according to the used material.

In addition, the light emitting efficiency ($Eff_{0.1}$) measured at a current density of 0.1 mA/cm$^2$; and the light emitting efficiency ($Eff_{10}$) measured at a current density of 10 mA/cm² for the organic light emitting device according to the present invention satisfies Mathematical Formula 1 below.

$$(Eff_{10}-Eff_{0.1})/Eff_{0.1} \leq 0.20 \quad \text{[Mathematical Formula 1]}$$

As described above, the change in the efficiency caused by the current density is small, thereby preventing the panel failure and exhibiting the long lifetime.

The production of the above-mentioned organic light emitting device of the present invention will be described in detail by way of the following examples. However, these examples are given for illustrative purposes only, and these examples are not intended to limit the scope of the invention in any way.

Preparation Example 1-1: Preparation of Compound 1-1

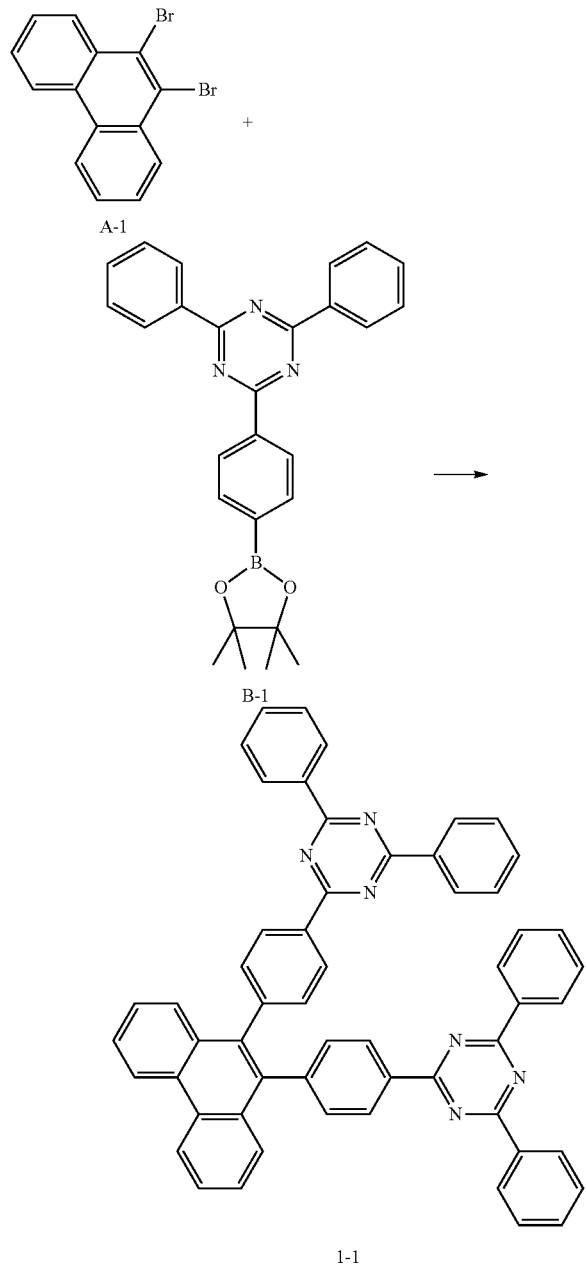

The compound A-1 (10 g, 29.8 mmol) and the compound B-1 (25.9 g, 59.6 mmol) were added to dioxane (150 mL). 2M K₃PO₄ (100 mL), Pd(dba)₂ (1.2 g), and PCy₃ (1.2 g) were added thereto, followed by stirring and refluxing for 6 hours. After cooling down to room temperature, the mixture was filtrated, and the resulting solid was recrystallized from chloroform and ethanol to give the compound 1-1 (15.6 g, yield 66%, MS: [M+H]⁺=793).

Preparation Example 1-2: Preparation of Compound 1-2

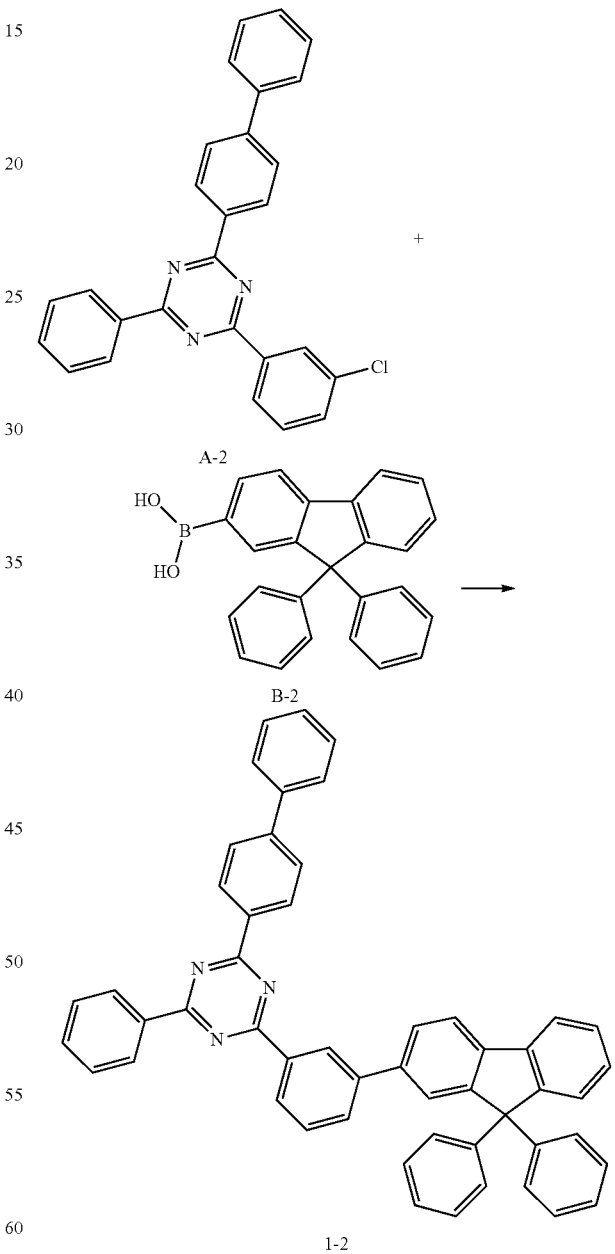

The compound A-2 (10 g, 23.8 mmol) and the compound B-2 (8.63 g, 23.8 mmol) were added to dioxane (150 mL). 2M K₃PO₄ (100 mL), Pd(dba)₂ (0.6 g), and PCy₃ (0.6 g) were added thereto, followed by stirring and refluxing for 10 hours. After cooling down to room temperature, the mixture was filtrated, and the resulting solid was recrystallized from chloroform and ethanol to give the compound 1-2 (12.5 g, yield 75%, MS: [M+H]⁺=702).

Preparation Example 1-3: Preparation of Compound 1-3

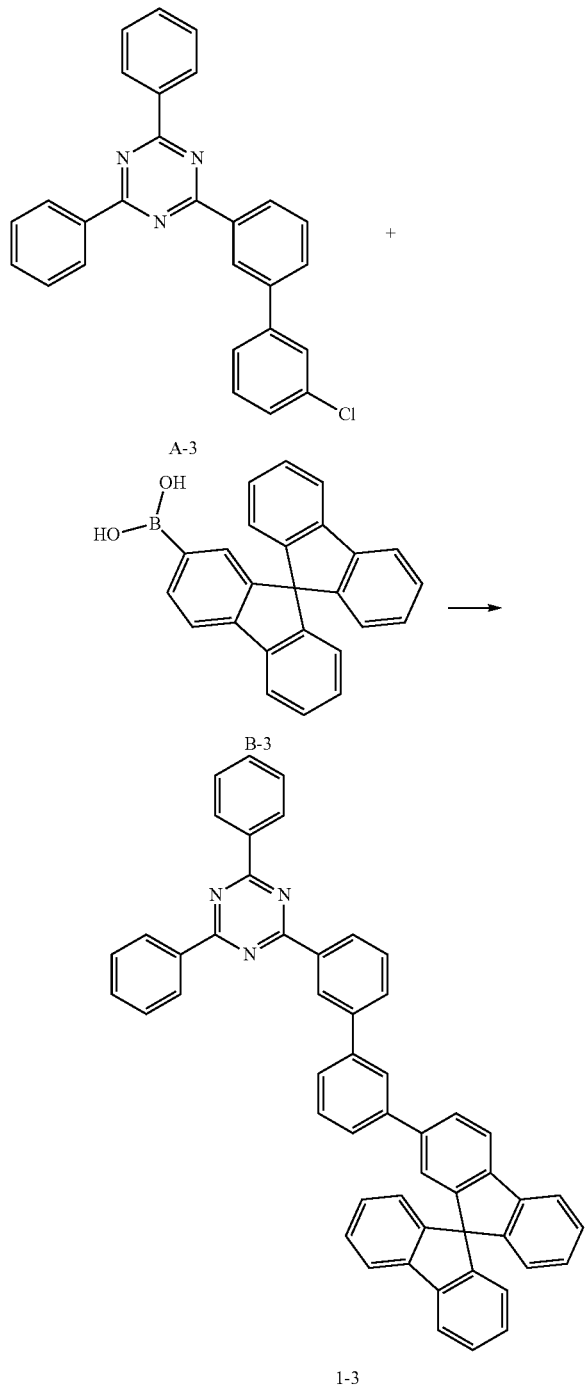

The compound A-3 (10 g, 23.8 mmol) and the compound B-3 (8.58 g, 23.8 mmol) were added to dioxane (150 mL). 2M K₃PO₄ (100 mL), Pd(dba)₂ (0.6 g), and PCy₃ (0.6 g) were added thereto, followed by stirring and refluxing for 12 hours. After cooling down to room temperature, the mixture was filtrated, and the resulting solid was recrystallized from chloroform and ethanol to give the compound 1-3 (11.3 g, yield 71%, MS: [M+H]⁺=670).

Preparation Example 1-4: Preparation of Compound 1-4

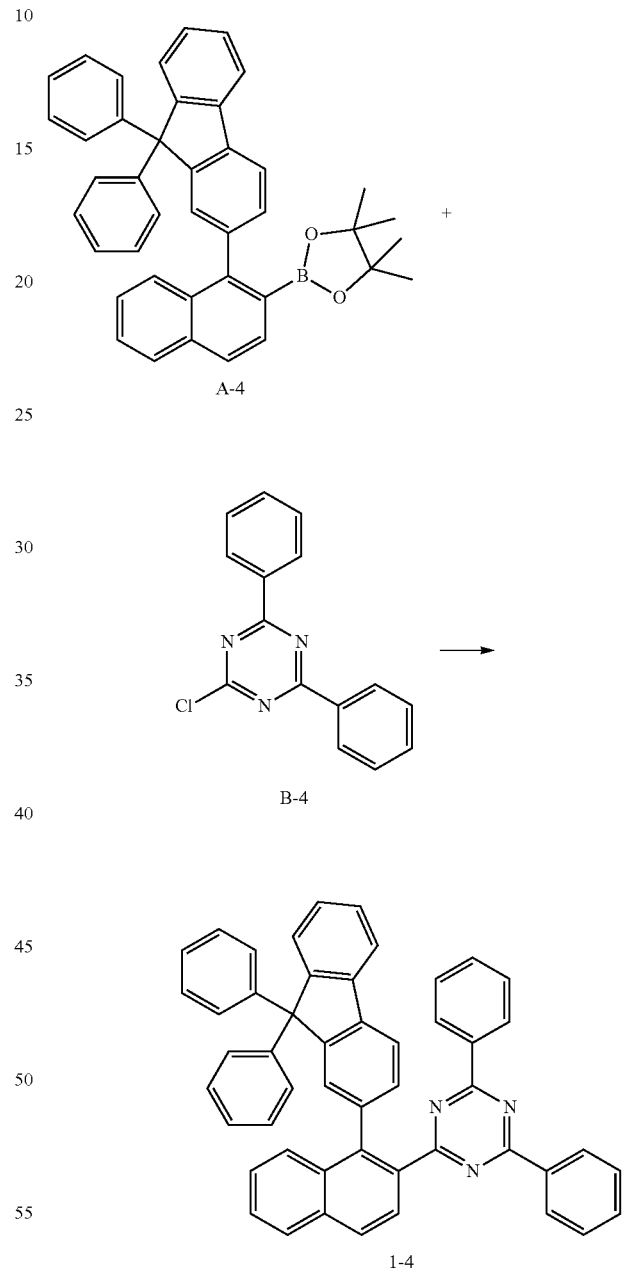

The compound A-4 (10 g, 17.5 mmol) and the compound B-4 (4.69 g, 17.5 mmol) were added to tetrahydrofuran (150 mL). 2M K₂CO₃ (100 mL), Pd(dba)₂ (0.6 g), and PCy₃ (0.6 g) were added thereto, followed by stirring and refluxing for 6 hours. After cooling down to room temperature, the mixture was filtrated, and the resulting solid was recrystallized from chloroform and ethanol to give the compound 1-4 (9.69 g, yield 82%, MS:[M+H]⁺=676).

Preparation Example 1-5: Preparation of Compound 1-5

Preparation Example 1-6: Preparation of Compound 1-6

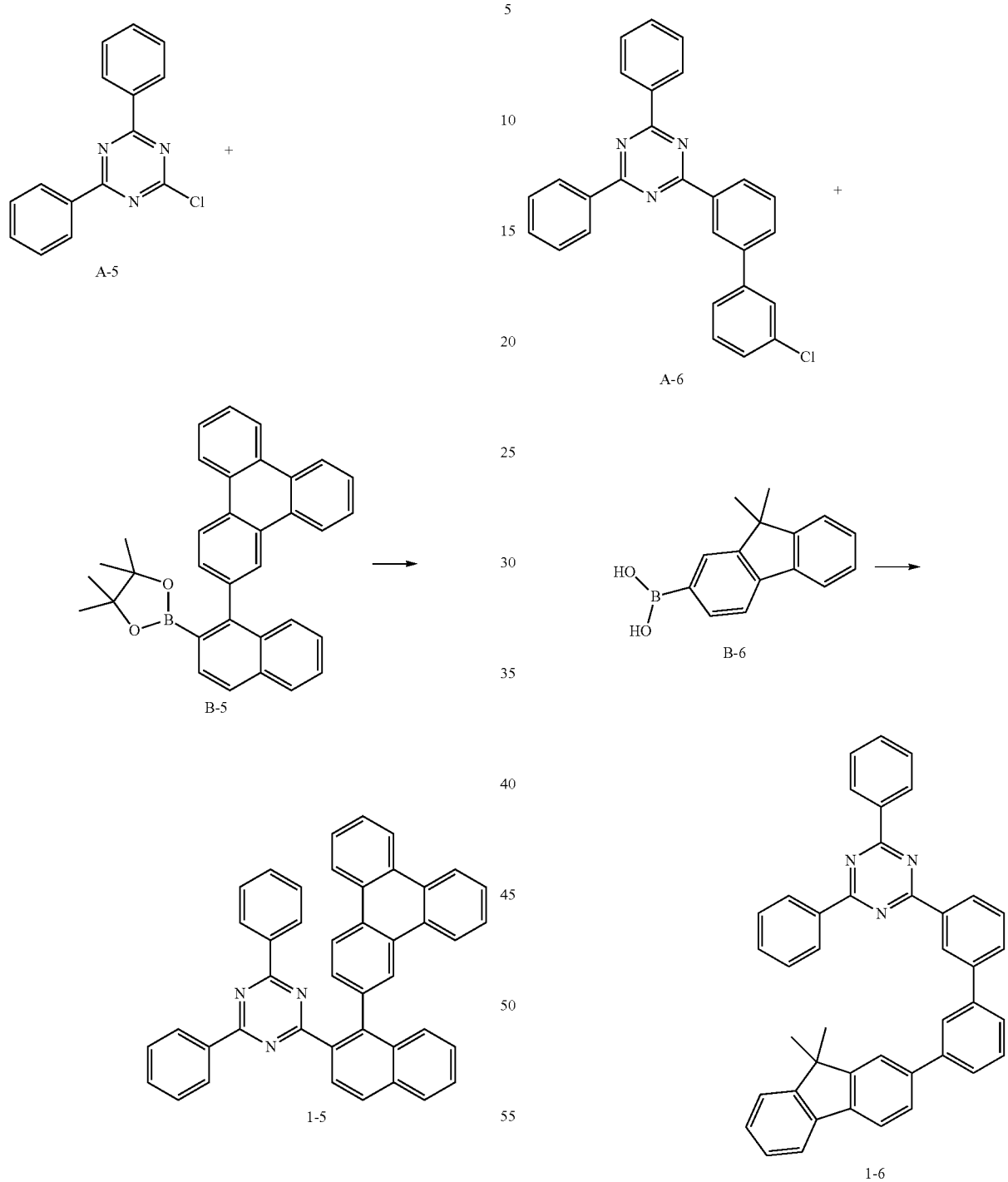

The compound A-5 (10 g, 37.3 mmol) and the compound B-5 (17.9 g, 37.3 mmol) were added to tetrahydrofuran (150 mL). 2M K$_2$CO$_3$ (100 mL), Pd(dba)$_2$ (0.6 g), and PCy$_3$ (0.6 g) were added thereto, followed by stirring and refluxing for 8 hours. After cooling down to room temperature, the mixture was filtrated, and the resulting solid was recrystallized from chloroform and ethanol to give the compound 1-5 (17.3 g, yield 79%, MS:[M+H]$^+$=586).

The compound A-6 (10 g, 23.8 mmol) and the compound B-6 (5.67 g, 23.8 mmol) were added to dioxane (150 mL). 2M K$_3$PO$_4$ (100 mL), Pd(dba)$_2$ (0.6 g), and PCy$_3$ (0.6 g) were added thereto, followed by stirring and refluxing for 16 hours. After cooling down to room temperature, the mixture was filtrated, and the resulting solid was recrystallized from chloroform and ethanol to give the compound 1-6 (10.3 g, yield 75%, MS: [M+H]$^+$=578).

Preparation Example 2-1: Preparation of Compound 2-1

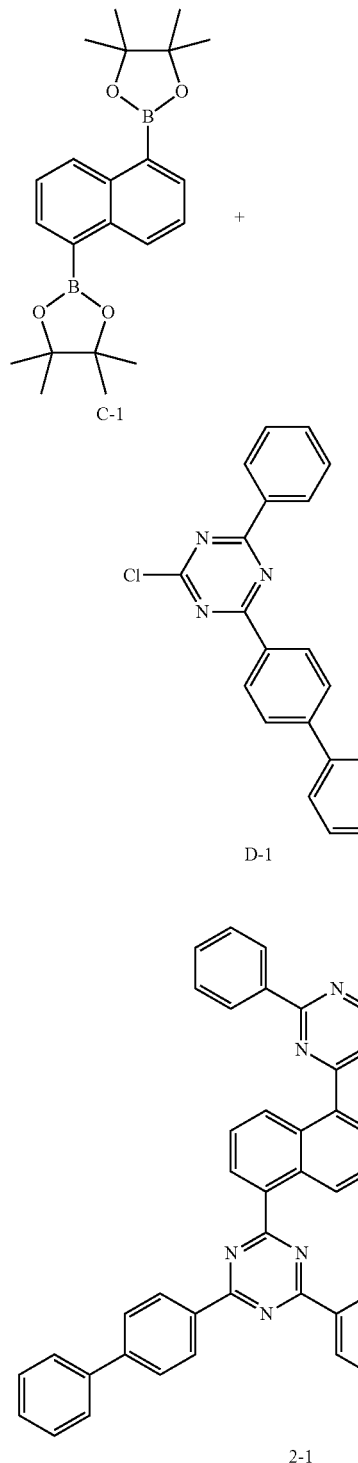

The compound C-1 (10 g, 26.3 mmol) and the compound D-1 (18.1 g, 52.6 mmol) were added to dioxane (150 mL). 2M K$_3$PO$_4$ (100 mL), Pd(dba)$_2$ (1.2 g), and PCy$_3$ (1.2 g) were added thereto, followed by stirring and refluxing for 15 hours. After cooling down to room temperature, the mixture was filtrated, and the resulting solid was recrystallized from chloroform and ethanol to give the compound 2-1 (13.9 g, yield 71%, MS: [M+H]$^+$743).

Preparation Example 2-2: Preparation of Compound 2-2

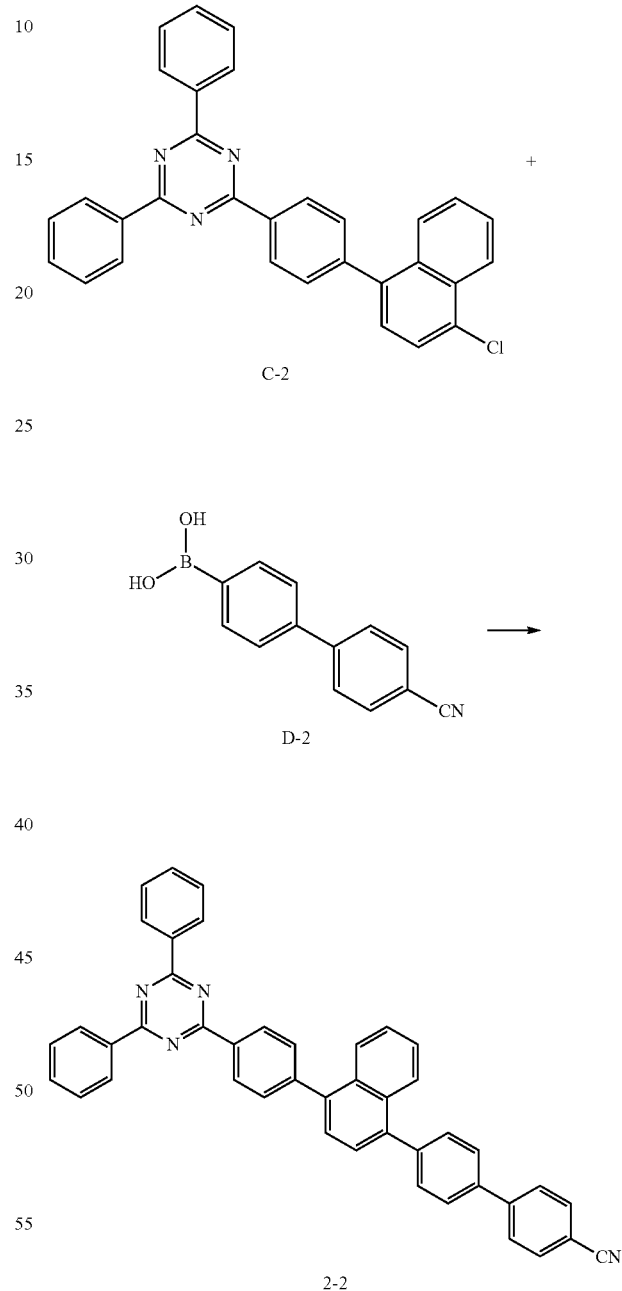

The compound C-2 (10 g, 21.3 mmol) and the compound D-2 (4.75 g, 52.6 mmol) were added to dioxane (150 mL). 2M K$_3$PO$_4$ (100 mL), Pd(dba)$_2$ (0.6 g), and PCy$_3$ (0.6 g) were added thereto, followed by stirring and refluxing for 13 hours. After cooling down to room temperature, the mixture was filtrated, and the resulting solid was recrystallized from chloroform and ethanol to give the compound 2-2 (9.53 g, yield 73%, MS: [M+H]$^+$=613).

Preparation Example 2-3: Preparation of Compound 2-3

Preparation Example 2-4: Preparation of Compound 2-4

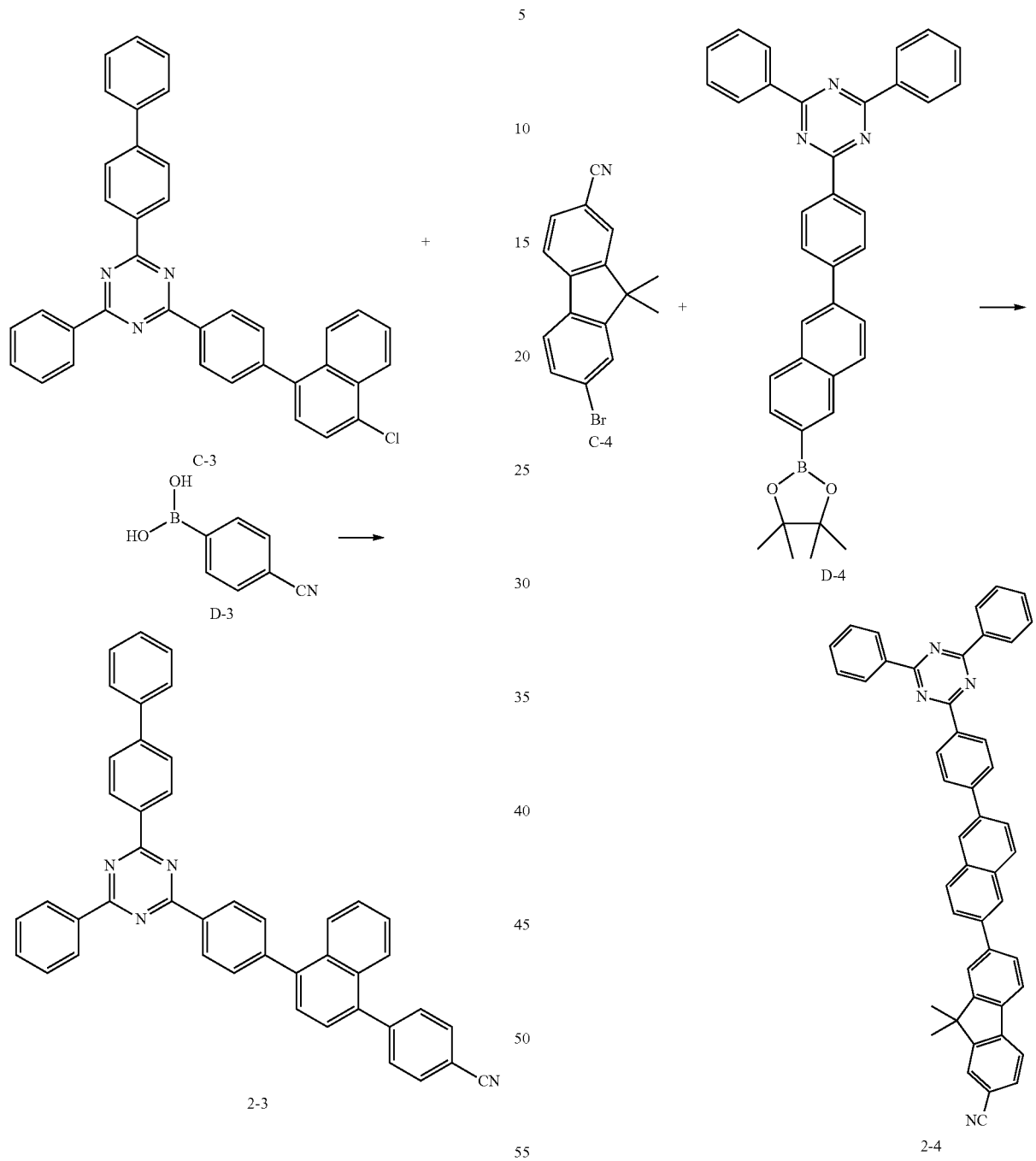

The compound C-3 (10 g, 18.3 mmol) and the compound D-3 (2.69 g, 18.3 mmol) were added to dioxane (150 mL). 2M $K_3PO_4$ (100 mL), Pd(dba)$_2$ (0.6 g), and PCy$_3$ (0.6 g) were added thereto, followed by stirring and refluxing for 10 hours. After cooling down to room temperature, the mixture was filtrated, and the resulting solid was recrystallized from chloroform and ethanol to give the compound 2-3 (7.40 g, yield 66%, MS: [M+H]$^+$=613).

The compound C-4 (7 g, 23.5 mmol) and the compound D-4 (13.2 g, 23.5 mmol) were added to tetrahydrofuran (150 mL). 2M $K_2CO_3$ (100 mL), Pd(dba)$_2$ (0.6 g), and PCy$_3$ (0.6 g) were added thereto, followed by stirring and refluxing for 5 hours. After cooling down to room temperature, the mixture was filtrated, and the resulting solid was recrystallized from chloroform and ethanol to give the compound 2-4 (11.2 g, yield 73%, MS:[M+H]$^+$653).

Preparation Example 2-5: Preparation of Compound 2-5

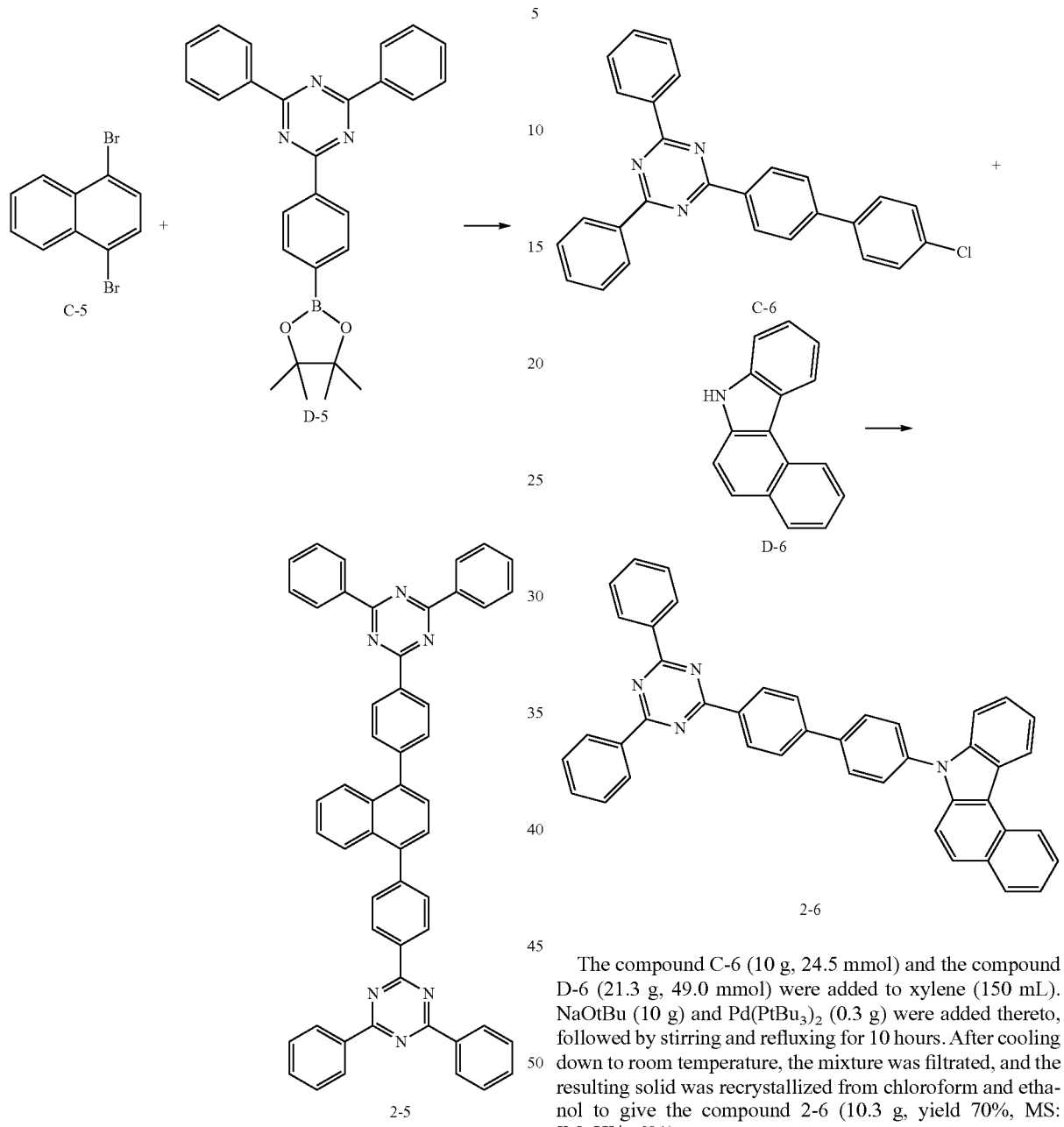

The compound C-5 (7 g, 24.5 mmol) and the compound D-5 (21.3 g, 49.0 mmol) were added to dioxane (150 mL). 2M K$_3$PO$_4$ (100 mL), Pd(dba)$_2$ (1.1 g), and PCy$_3$ (1.1 g) were added thereto, followed by stirring and refluxing for 10 hours. After cooling down to room temperature, the mixture was filtrated, and the resulting solid was recrystallized from chloroform and ethanol to give the compound 2-5 (12.0 g, yield 75%, MS: [M+H]$^+$=653).

Preparation Example 2-6: Preparation of Compound 2-6

The compound C-6 (10 g, 24.5 mmol) and the compound D-6 (21.3 g, 49.0 mmol) were added to xylene (150 mL). NaOtBu (10 g) and Pd(PtBu$_3$)$_2$ (0.3 g) were added thereto, followed by stirring and refluxing for 10 hours. After cooling down to room temperature, the mixture was filtrated, and the resulting solid was recrystallized from chloroform and ethanol to give the compound 2-6 (10.3 g, yield 70%, MS: [M+H]$^+$=601).

EXAMPLE

Example 1

A glass substrate on which a thin film of ITO (indium tin oxide) was coated in a thickness of 1,300 Å was put into distilled water containing the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound HI-1 described below was vacuum-deposited in a thicknesses of 600 Å to form the hole injection layer. A compound of HAT-CN (50 Å) and a compound HT-A (600 Å) described below were sequentially vacuum-deposited on the hole injection layer to form a hole transport layer. Then, a compound BH and a compound BO were deposited under vacuum at a weight ratio of 25:1 in a thicknesses of 200 Å on the hole transport layer to form a light emitting layer. The compound 1-1 previously prepared was vacuum-deposited on the light emitting layer in a thickness of 50 Å to form a power efficiency enhancement layer. The compound 2-1 and LiQ(8-hydroxyquinolato lithium) were deposited at a weight ratio of 1:1 in a thicknesses of 300 Å on the power efficiency enhancement layer to form a gradation enhancement layer. Lithium fluoride (LiF) in a thickness of 10 Å and aluminum in a thickness of 1,000 Å were sequentially deposited on the gradation enhancement layer to form a cathode.

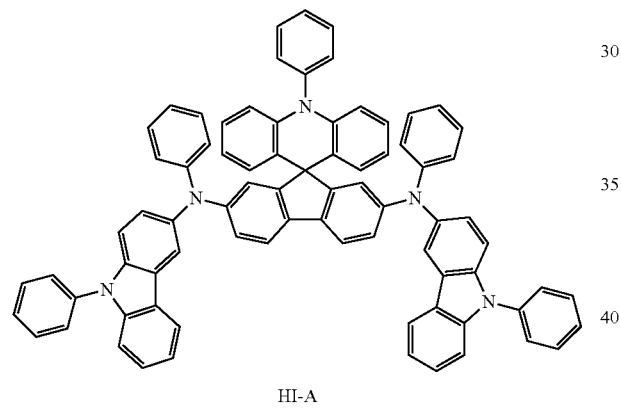

HI-A

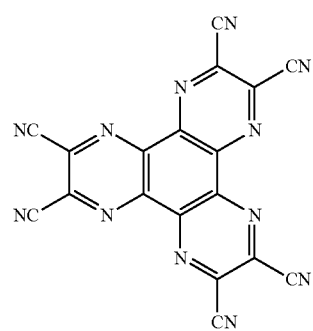

HAT-CN

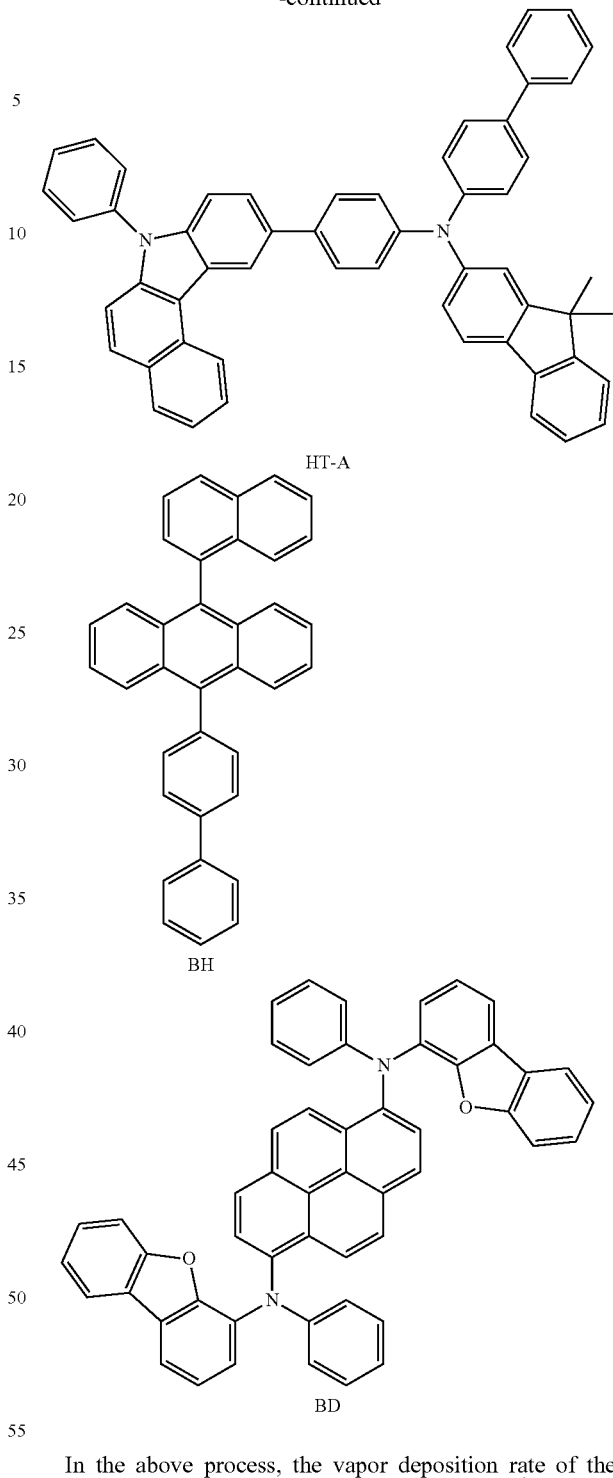

In the above process, the vapor deposition rate of the organic material was maintained at 0.4 to 0.7 Å/sec, the deposition rate of the lithium fluoride was maintained at 0.3 Å/sec, the deposition rate of aluminum was maintained at 2 Å/sec, and the degree of vacuum during vapor deposition was maintained at $1\times10^{-7}\sim5\times10^{-8}$ torr, thereby producing an organic light emitting device.

Examples 2 to 16

The organic light emitting devices were manufactured in the same manner as in Example 1, except that the compounds shown in Table 1 below were respectively used instead of the compound 1-1 and the compound 2-1.

Comparative Examples 1 to 4

The organic light emitting devices were manufactured in the same manner as in Example 1, except that the compounds shown in Table 1 below were respectively used instead of the compound 1-1 and the compound 2-1. In Table 1 below, the compound ET-1-A is as follows.

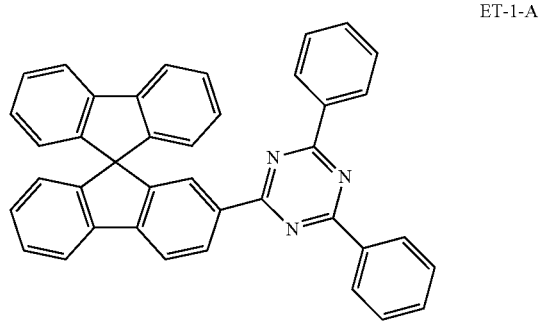 [SMILES: c1ccc(-c2nc(-c3ccccc3)nc(-c3ccc4c(c3)C3(c5ccccc5-c5ccccc53)c3ccccc3-4)n2)cc1]

ET-1-A

Experimental Example

The driving voltage and the light emitting efficiency of the organic light emitting devices manufactured by the aforementioned method were measured at a current density of 0.1 mA/cm$^2$ or 10 mA/cm$^2$, and the time (LT90) at which luminance was 90% of initial luminance was measured at the current density of 20 mA/cm$^2$. The result is described in Table 1 below.

Table 2 below shows the comparison of the difference in efficiency between the current densities of 0.1 mA/cm$^2$ and 10 mA/cm$^2$ measured previously.

TABLE 2

|  | Difference in efficiency (Cd/A) | % Conversion |
|---|---|---|
| Ex. 1 | 0.18 | 3.5 |
| Ex. 2 | 0.35 | 6.8 |
| Ex. 3 | 0.04 | 0.8 |
| Ex. 4 | 0.11 | 2.0 |
| Ex. 5 | 0.19 | 3.6 |
| Ex. 6 | 0.35 | 6.2 |
| Ex. 7 | 0.25 | 4.4 |
| Ex. 8 | 0.14 | 2.6 |
| Ex. 9 | 0.06 | 1.1 |
| Ex. 10 | 0.16 | 3.0 |
| Ex. 11 | 0.30 | 5.3 |
| Ex. 12 | 0.28 | 4.9 |
| Ex. 13 | 0.47 | 8.1 |
| Ex. 14 | 0.06 | 1.2 |
| Ex. 15 | 0.31 | 6.1 |
| Ex. 16 | 0.30 | 5.8 |
| Comparative Ex. 1 | 0.81 | 17.9 |
| Comparative Ex. 2 | 0.74 | 13.2 |
| Comparative Ex. 3 | 1.30 | 30.1 |
| Comparative Ex. 4 | 0.04 | 1.0 |

The OLED device is a current-driven device, and the luminance (nit) caused by the current density is linearly displayed. In such an OLED device, the change in efficiency caused by the luminance (nit) must be small so that the expression of color due to the luminance of the display panel is uniformly displayed. If the change in the efficiency due to the luminance (nit) is large, the color in the panel changes depending on the luminance, which causes the panel failure. In order to solve these problems, if the gradation enhancement layer (GEL) and the power efficiency enhancement

TABLE 1

|  | Compound | | | Efficiency (Cd/A) | | | |  |
|---|---|---|---|---|---|---|---|---|
|  | power efficiency enhancement layer | gradation enhancement layer | Voltage(V) @10 mA/cm$^2$ | @0.1 mA/cm$^2$ | @10 mA/cm$^2$ | Color coordinate (x, y) | Life time (T90; hr) @20 mA/cm$^2$ |
| Ex. 1 | 1-1 | 2-1 | 3.74 | 5.16 | 5.34 | (0.134, 0.118) | 301 |
| Ex. 2 | 1-1 | 2-2 | 3.59 | 5.18 | 5.53 | (0.133, 0.117) | 335 |
| Ex. 3 | 1-2 | 2-2 | 3.81 | 5.32 | 5.36 | (0.134, 0.118) | 368 |
| Ex. 4 | 1-2 | 2-3 | 3.68 | 5.53 | 5.42 | (0.133, 0.118) | 321 |
| Ex. 5 | 1-3 | 2-2 | 3.76 | 5.28 | 5.47 | (0.134, 0.119) | 345 |
| Ex. 6 | 1-3 | 2-3 | 3.55 | 5.62 | 5.27 | (0.134, 0.117) | 310 |
| Ex. 7 | 1-3 | 2-4 | 3.51 | 5.72 | 5.47 | (0.134, 0.118) | 321 |
| Ex. 8 | 1-3 | 2-6 | 3.75 | 5.45 | 5.31 | (0.134, 0.118) | 311 |
| Ex. 9 | 1-4 | 2-2 | 3.68 | 5.32 | 5.38 | (0.133, 0.118) | 395 |
| Ex. 10 | 1-4 | 2-4 | 3.52 | 5.42 | 5.26 | (0.134, 0.117) | 389 |
| Ex. 11 | 1-5 | 2-2 | 3.59 | 5.62 | 5.32 | (0.134, 0.118) | 365 |
| Ex. 12 | 1-5 | 2-4 | 3.66 | 5.75 | 5.47 | (0.133, 0.118) | 356 |
| Ex. 13 | 1-5 | 2-5 | 3.55 | 5.82 | 5.35 | (0.133, 0.118) | 292 |
| Ex. 14 | 1-6 | 2-2 | 3.81 | 5.16 | 5.22 | (0.134, 0.119) | 416 |
| Ex. 15 | 1-6 | 2-4 | 3.61 | 5.07 | 5.38 | (0.133, 0.117) | 385 |
| Ex. 16 | 1-6 | 2-5 | 3.75 | 5.21 | 5.51 | (0.134, 0.118) | 352 |
| Comparative Ex. 1 | ET-1-A | 2-1 | 3.79 | 4.52 | 5.33 | (0.133, 0.118) | 233 |
| Comparative Ex. 2 | 1-1 | ET-1-A | 3.75 | 5.62 | 4.88 | (0.134, 0.119) | 252 |
| Comparative Ex. 3 | 1-1 | 1-1 | 3.48 | 4.32 | 5.62 | (0.133, 0.118) | 153 |
| Comparative Ex. 4 | 2-2 | 2-2 | 4.25 | 3.88 | 3.92 | (0.134, 0.118) | 352 | layer (PEEL) according to the present invention are applied at the same time, the change in the efficiency due to the luminance is displayed to be less than 10% and at the same time a device having high efficiency and long lifetime can be produced.

FIG. 3 is a graph showing a change in the efficiency caused by electric current in Example 1 and Comparative Example 1. As shown in FIG. 3, in Example 1, it was confirmed that the efficiency change at 0.1 mA/cm$^2$ and 10 mA/cm$^2$ was as small as 10% or less. In Comparative Example 1, it was confirmed that the difference in efficiency at 0.1 mA/cm$^2$ and 10 mA/cm$^2$ was displayed be 10% or more. It was confirmed that the difference between the maximum efficiency value and the minimum efficiency value was displayed to be 60% or more in Comparative Example 1. When the power efficiency enhancement layer and the gradation enhancement layer according to the present invention were used simultaneously, it was confirmed that the change in the color of the display panel due to the luminance can be minimized and the lifetime also increases.

| [Explanation of Sign] | |
|---|---|
| 1: substrate | 2: anode |
| 3: hole transport layer | 4: light emitting layer |
| 5: power efficiency enhancement layer | |
| 6: gradation enhancement layer | |
| 7: cathode | 8: electron injection layer |

The invention claimed is:
1. An organic light emitting device comprising:
a first electrode;
a hole transport layer;
a light emitting layer;
a power efficiency enhancement layer;
a gradation enhancement layer; and
a second electrode,
wherein the power efficiency enhancement layer comprises a compound represented by Chemical Formula 1 below, and
the gradation enhancement layer comprises a compound represented by Chemical Formula 2 below:

[Chemical Formula 1]

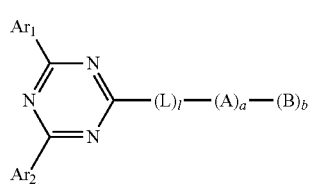

in Chemical Formula 1,
$Ar_1$ and $Ar_2$ are each independently a substituted or unsubstituted $C_{6-60}$ aryl; or a substituted or unsubstituted $C_{2-60}$ heteroaryl containing at least one of O, N, Si and S,
each L is independently a direct bond, or a substituted or unsubstituted $C_{6-60}$ arylene,
each A is independently a substituted or unsubstituted $C_{6-60}$ arylene having a meta- or ortho-linking group,
each B is independently a substituted or unsubstituted $C_{6-60}$ aryl; or a substituted or unsubstituted $C_{2-60}$ heteroaryl containing at least one of O, N, Si and S, l is an integer of 0 to 2,
a is an integer of 1 or 2, and
h is an integer of 1 or 2,

[Chemical Formula 2]

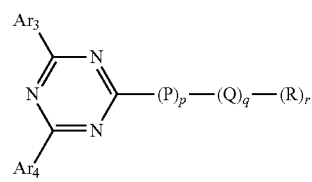

in Chemical Formula 2,
$Ar_3$ and $Ar_4$ are each independently a substituted or unsubstituted $C_{6-60}$ aryl; or a substituted or unsubstituted $C_{2-60}$ heteroaryl containing at least one of O, N, Si and S,
each P is independently a direct bond, or a substituted or unsubstituted $C_{6-60}$ arylene,
each Q is independently a substituted or unsubstituted $C_{6-60}$ arylene having a para-linking group,
each R is independently a substituted or unsubstituted $C_{6-60}$ aryl; or a substituted or unsubstituted $C_{2-60}$ heteroaryl containing at least one of O, N, Si and S,
p is an integer of 0 to 2,
q is an integer of 1 or 2, and
r is an integer of 1 or 2.
2. The organic light emitting device of claim 1,
wherein each A is independently selected from the group consisting of the following:

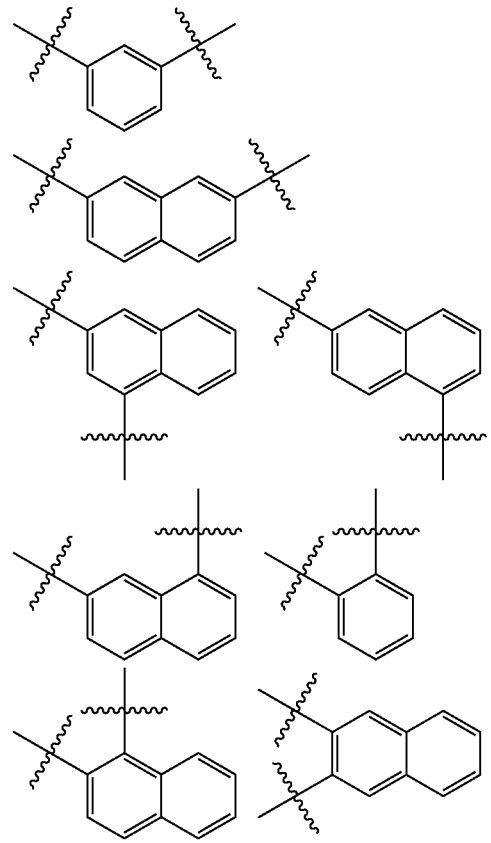

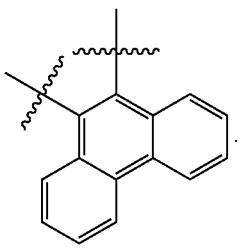

3. The organic light emitting device of claim 1, wherein Ar₁ and Ar₂ are each independently phenyl, biphenylyl, or naphthyl.

4. The organic light emitting device of claim 1, wherein L is a single bond, or phenylene.

5. The organic light emitting device of claim 1, wherein B is any one selected from the group consisting of the following:

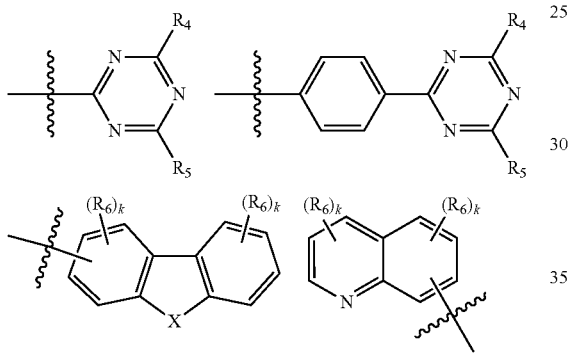

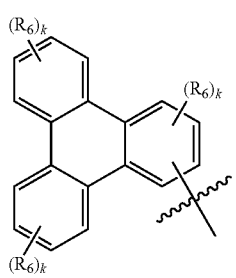

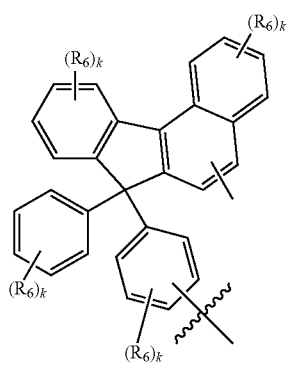

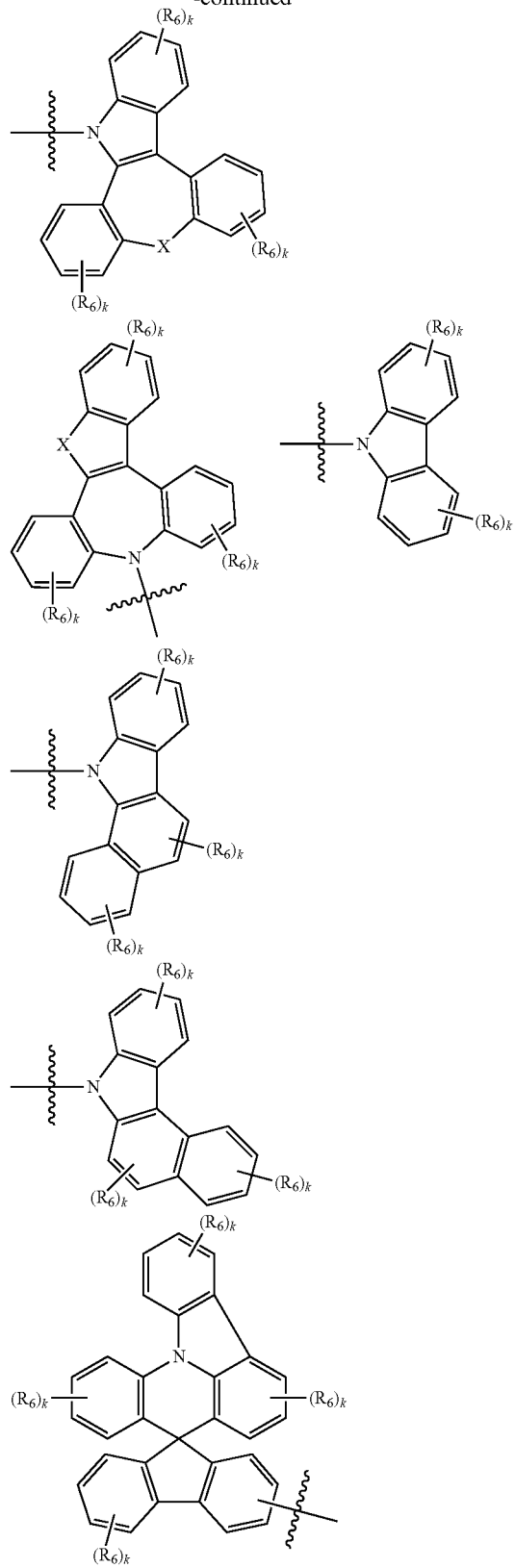

wherein,

R₄ to R₆ are each independently hydrogen; deuterium; halogen; cyano; nitro; amino; a substituted or unsubstituted $C_{1-60}$ alkyl; a $C_{1-60}$ haloalkyl; a substituted or unsubstituted $C_{1-60}$ haloalkoxy; a substituted or unsubstituted $C_{3-60}$ cycloalkyl; a substituted or unsubstituted $C_{2-60}$ alkenyl group; a substituted or unsubstituted $C_{6-60}$ aryl; or a substituted or unsubstituted $C_{6-60}$ heteroaryl containing at least one of O, N, Si and S, X is $CR_7R_8$, $NR_7$, S, or O, $R_7$ and $R_8$ are each independently a $C_{1-60}$ alkyl, or a $C_{6-60}$ aryl, or $R_7$ and $R_8$ together form a $C_{6-60}$ aromatic ring when X is $CR_7R_8$, and k is an integer of 0 to 2.

6. The organic light emitting device of claim 1, wherein each Q is independently selected from the group consisting of the following:

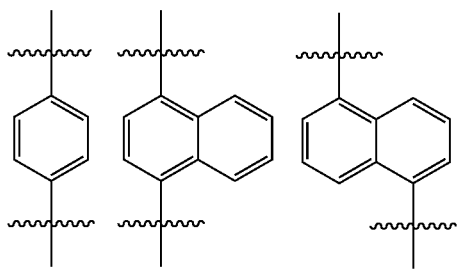

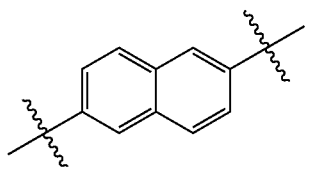

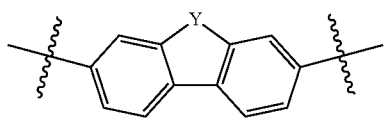

wherein,

Y is $CR'_1R'_2$, S, or O, and $R'_1$ and $R'_2$ are each independently a $C_{1-60}$ alkyl, or $C_{6-60}$ aryl, or $R'_1$ and $R'_2$ together form a $C_{6-60}$ aromatic ring.

7. The organic light emitting device of claim 1, wherein P is a single bond, or phenylene.

8. The organic light emitting device of claim 1, wherein R is any one selected from the group consisting of the following:

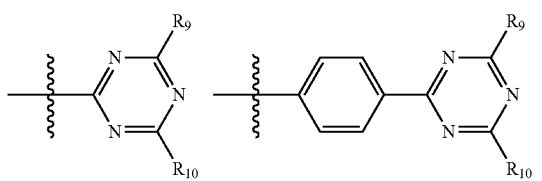

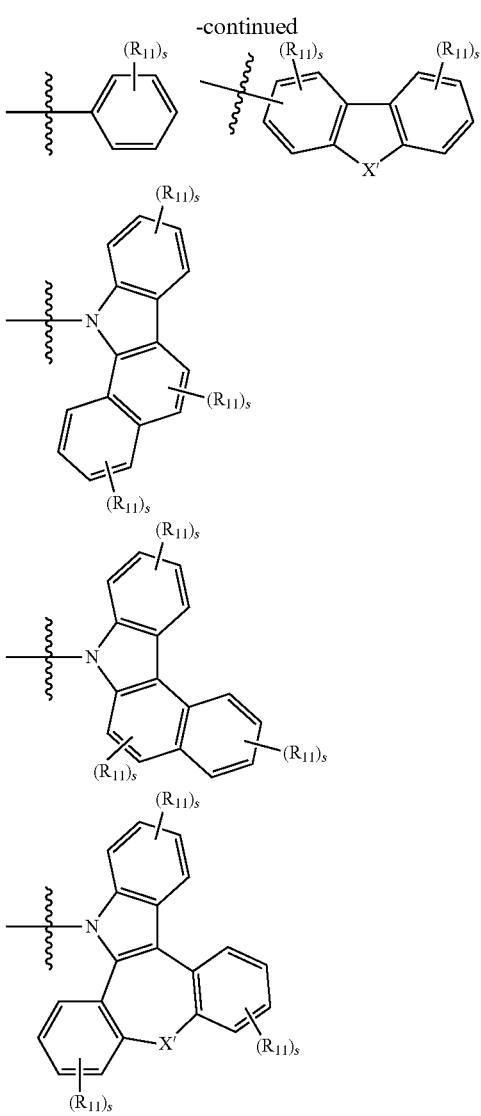

wherein, $R_9$ to $R_{11}$ are each independently hydrogen; deuterium; halogen; cyano; nitro; amino; a substituted or unsubstituted $C_{1-60}$ alkyl; a $C_{1-60}$ haloalkyl; a substituted or unsubstituted $C_{1-60}$ haloalkoxy; a substituted or unsubstituted $C_{3-60}$ cycloalkyl; a substituted or unsubstituted $C_{2-60}$ alkenyl group; a substituted or unsubstituted $C_{6-60}$ aryl; or a substituted or unsubstituted $C_{6-60}$ heteroaryl containing at least one of O, N, Si and S, X' is $CR_{12}R_{13}$, $NR_{12}$, S, or O, $R_{12}$ and $R_{13}$ are each independently a $C_{1-60}$ alkyl, or a $C_{6-60}$ aryl, or $R_{12}$ and $R_{13}$ together form a $C_{6-60}$ aromatic ring when X' is $CR_{12}R_{13}$, and s is an integer of 0 to 2.

9. The organic light emitting device of claim 1, wherein the compound represented by Chemical Formula 1 is any one selected from the group consisting of the following:

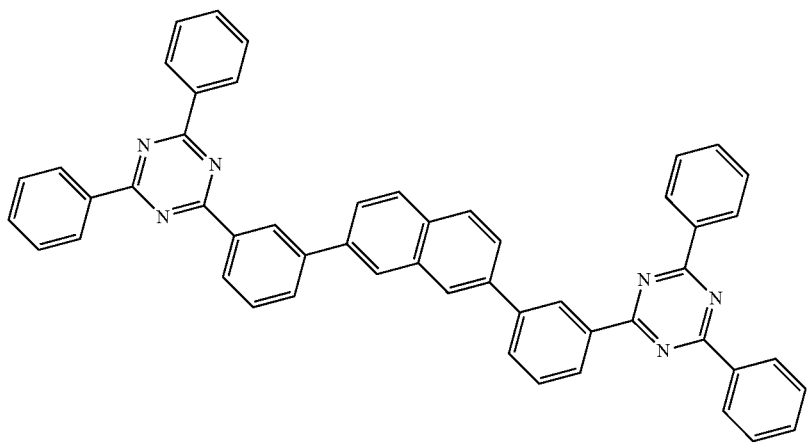
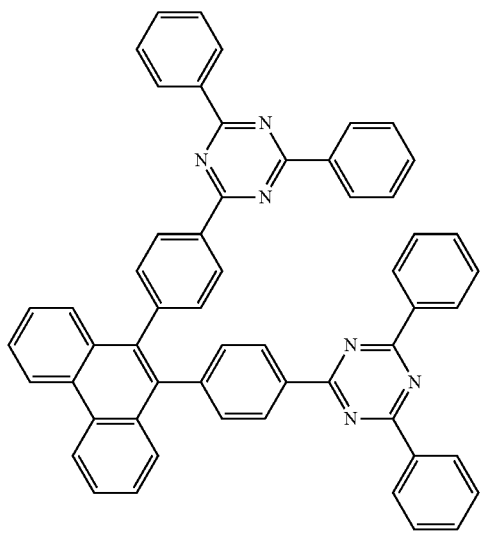
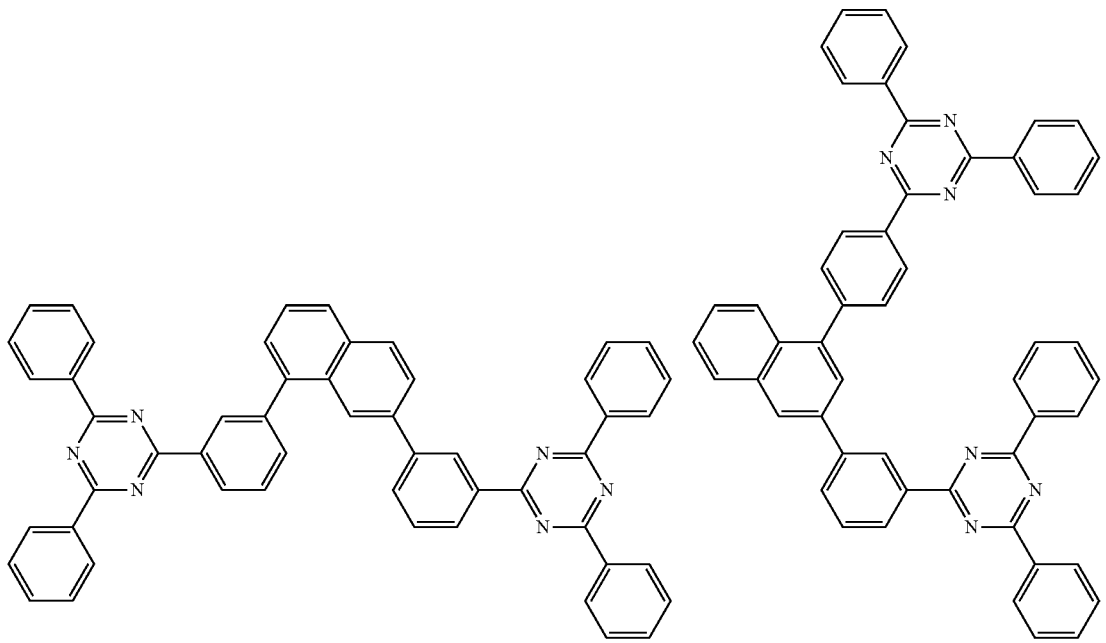

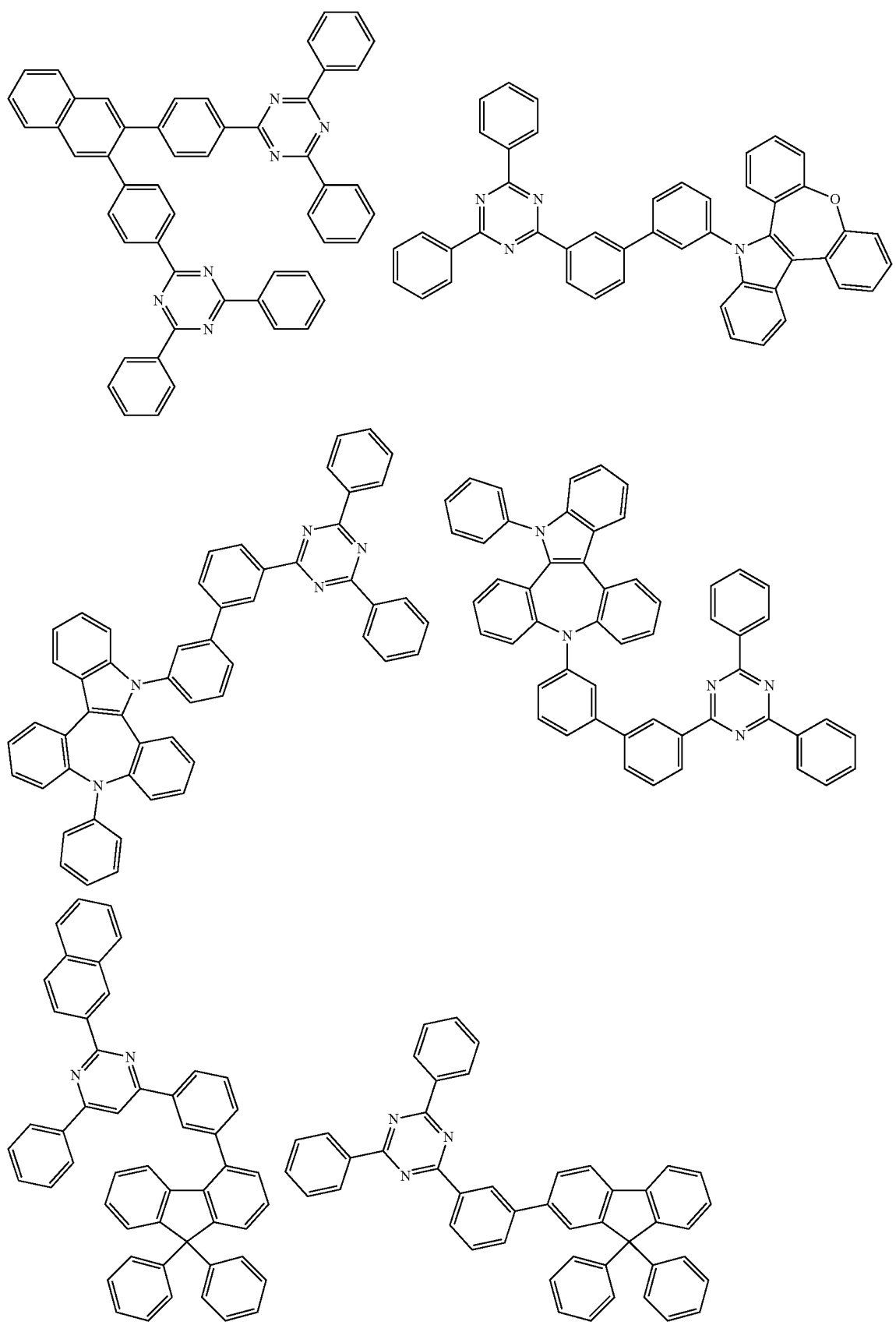

-continued
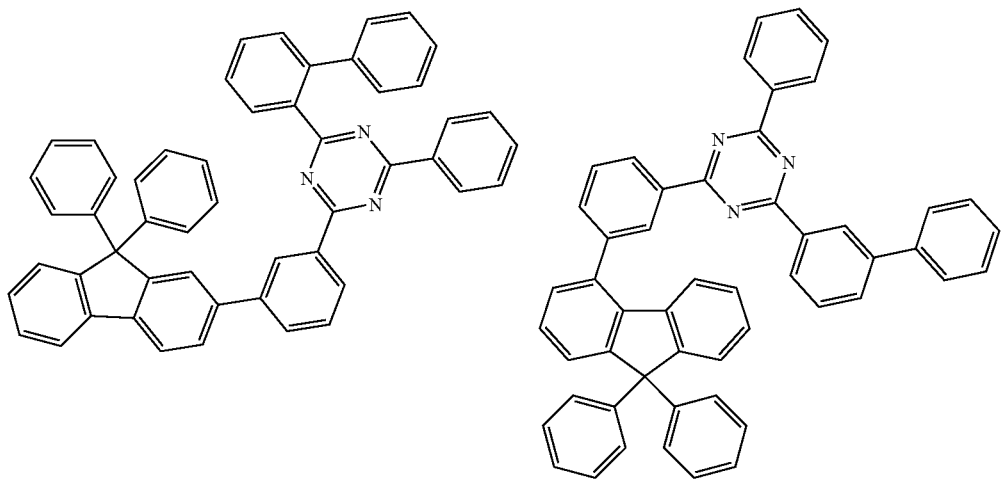
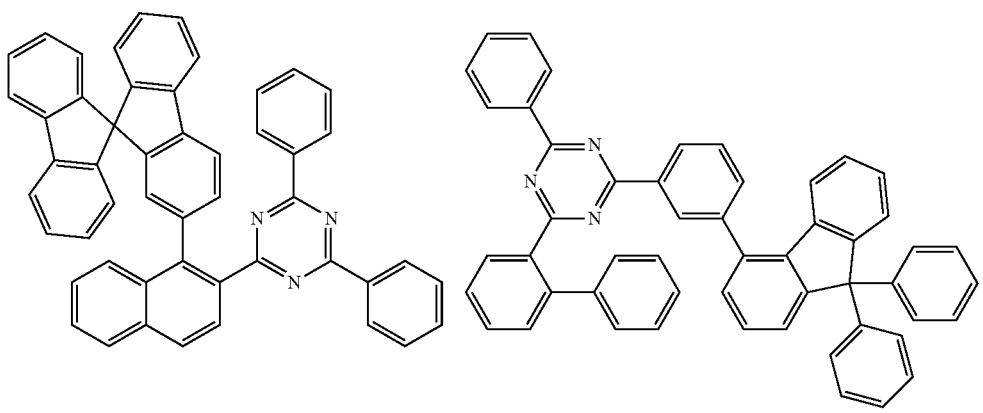
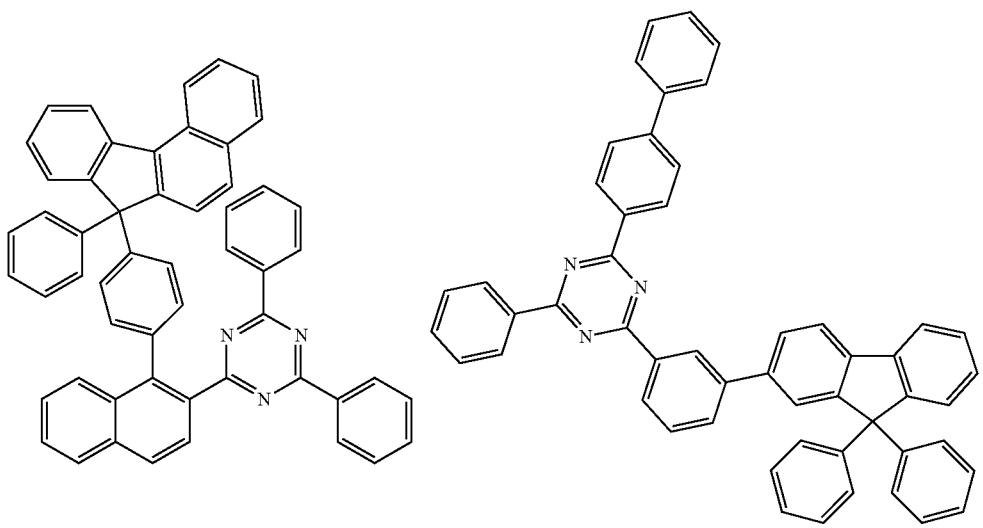

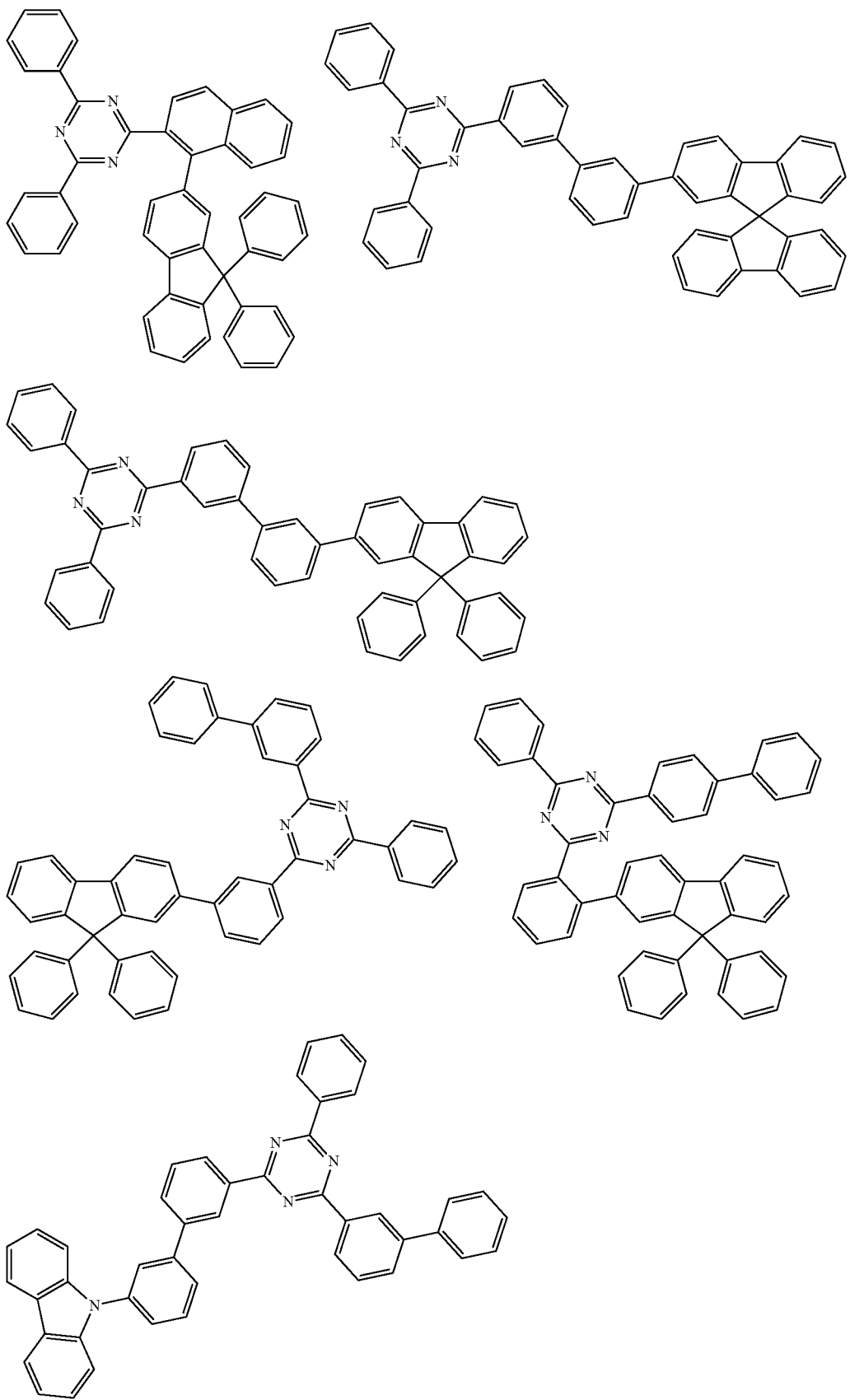

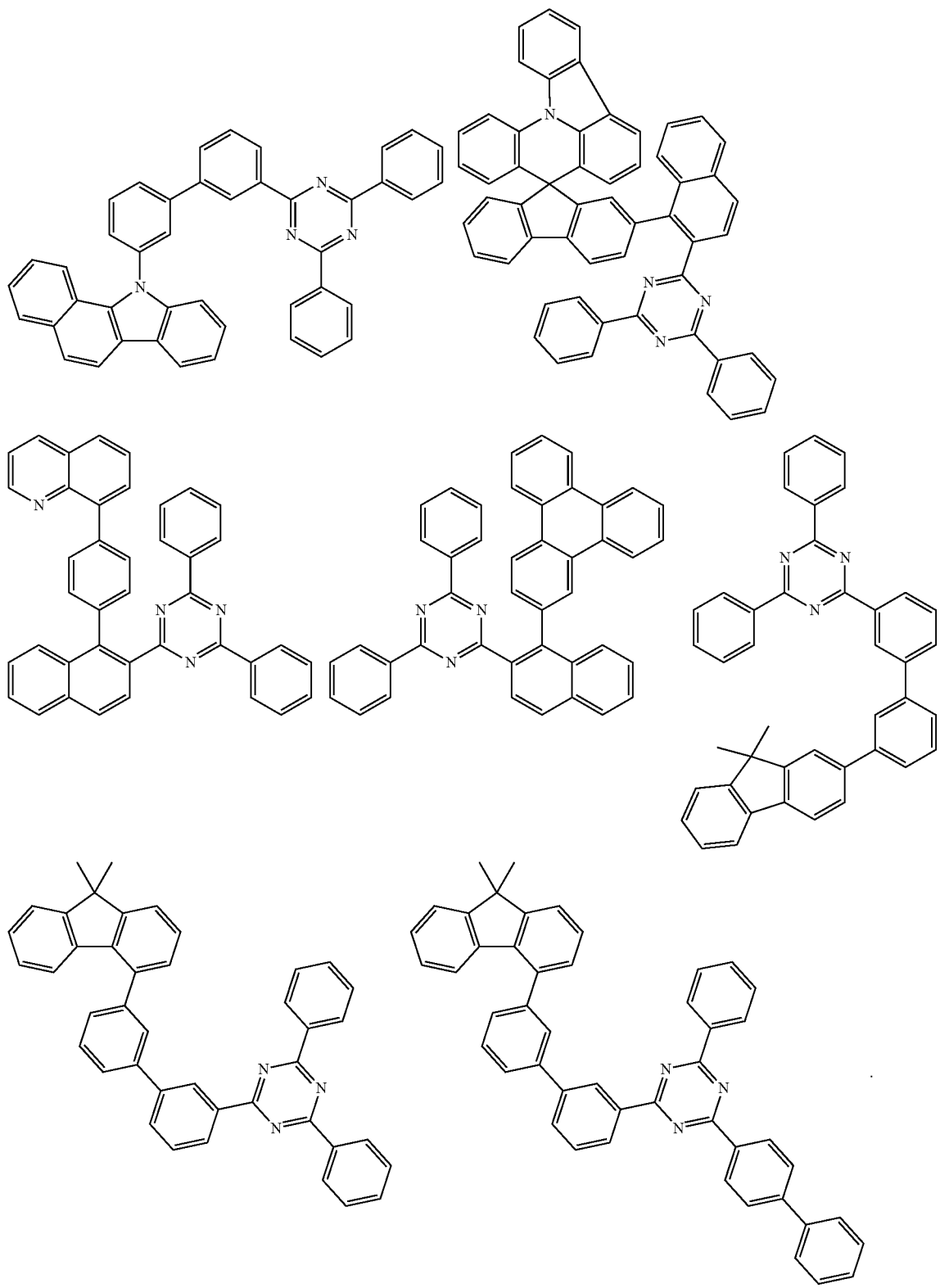

10. The organic light emitting device of claim 1, wherein the compound represented by Chemical Formula 2 is any one selected from the group consisting of the following:
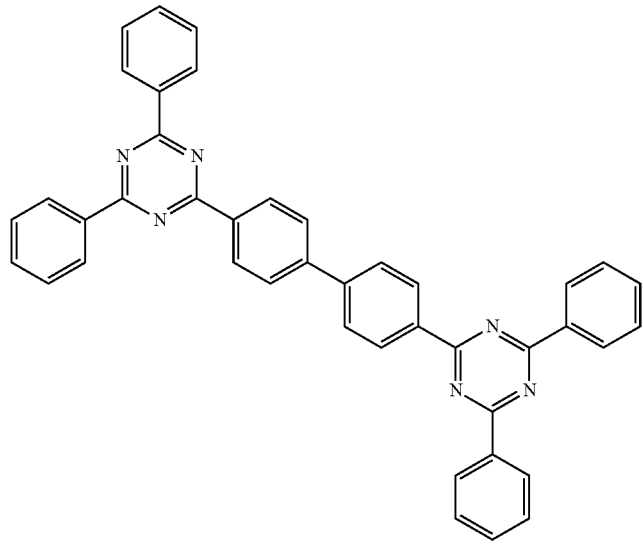
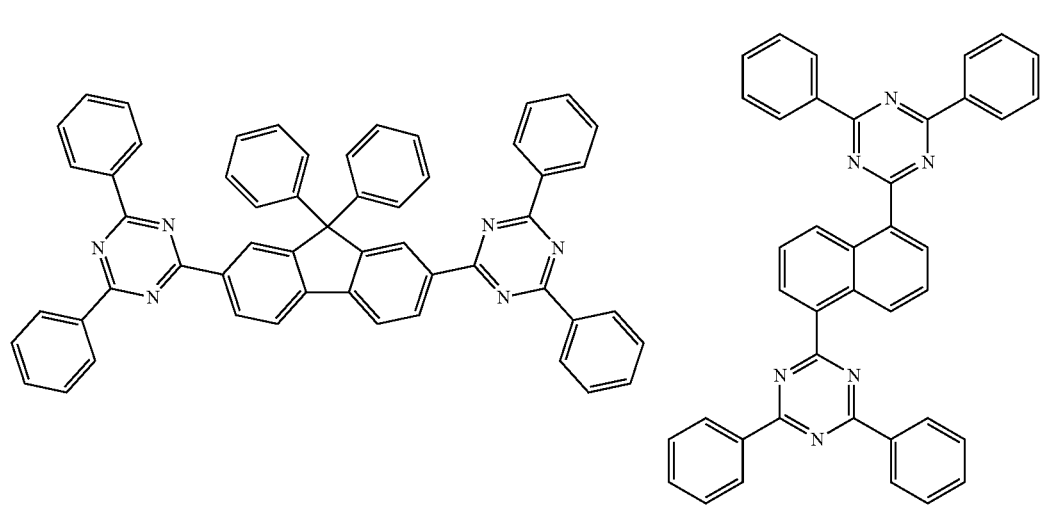

-continued
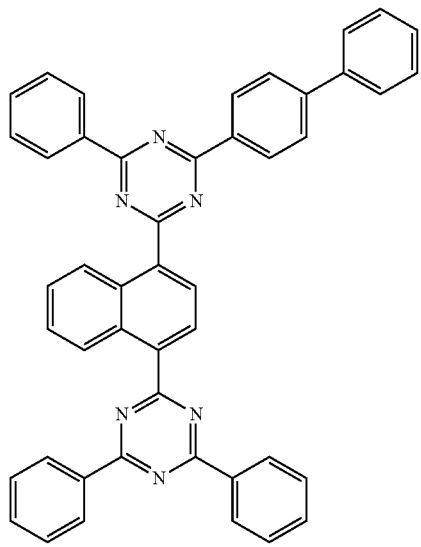
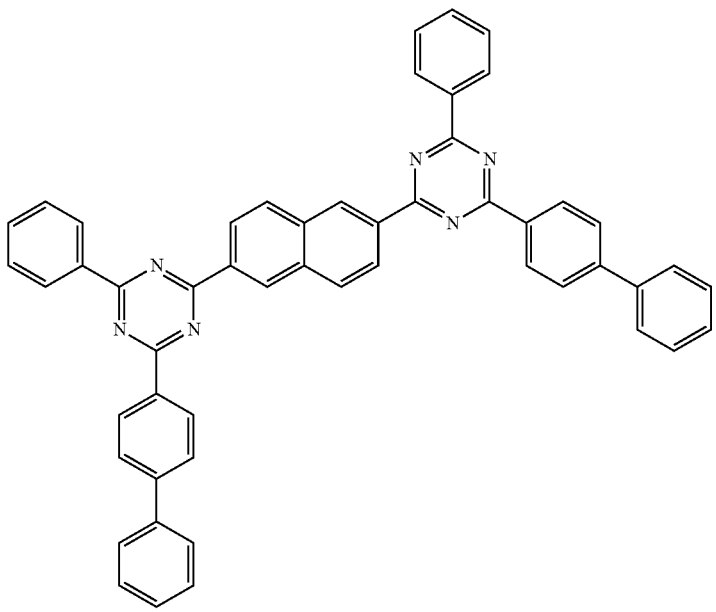
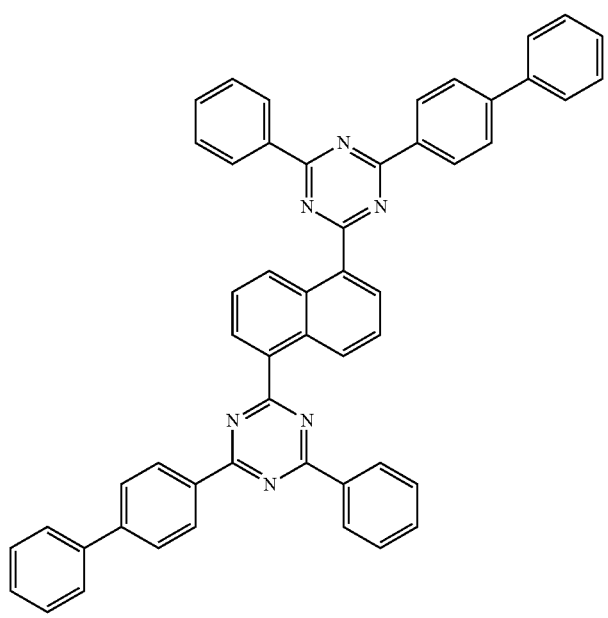

-continued
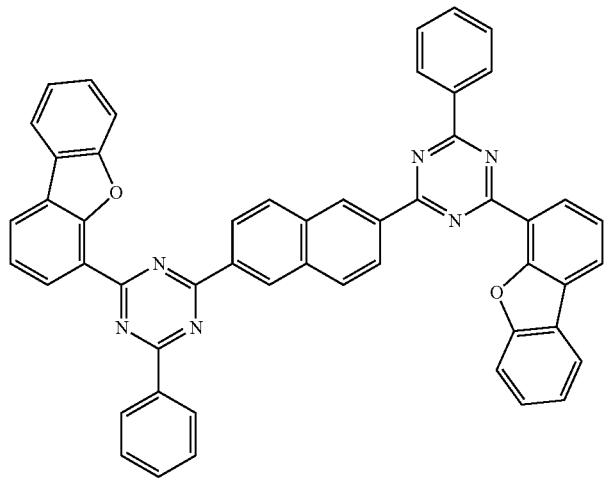
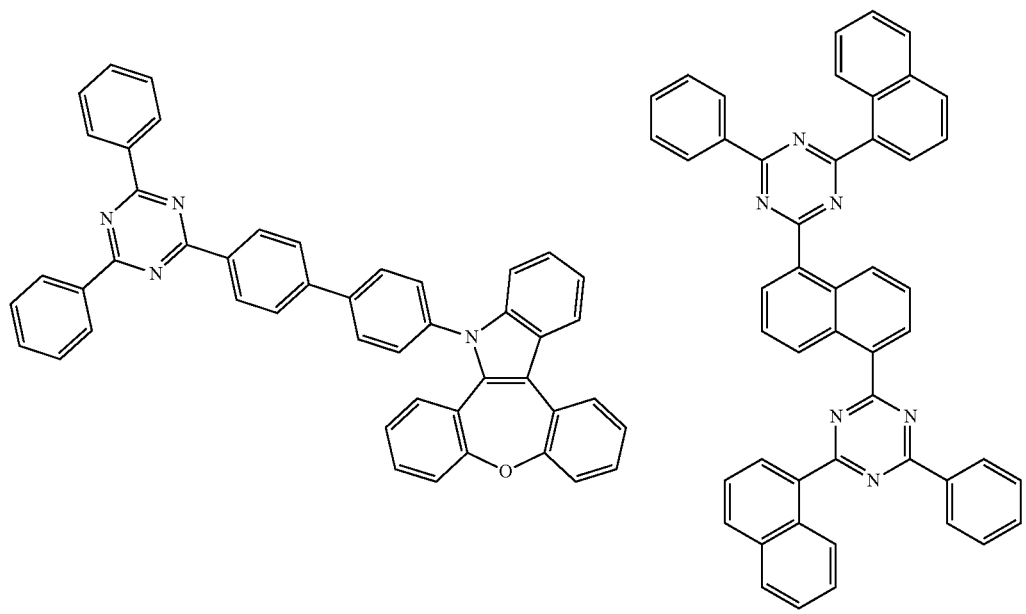
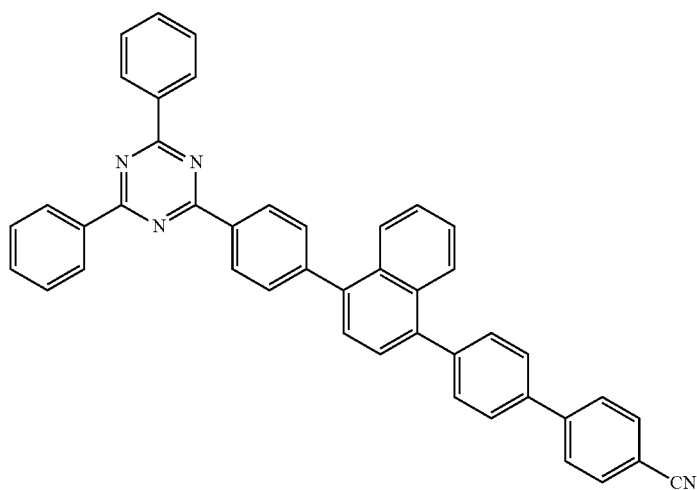

-continued
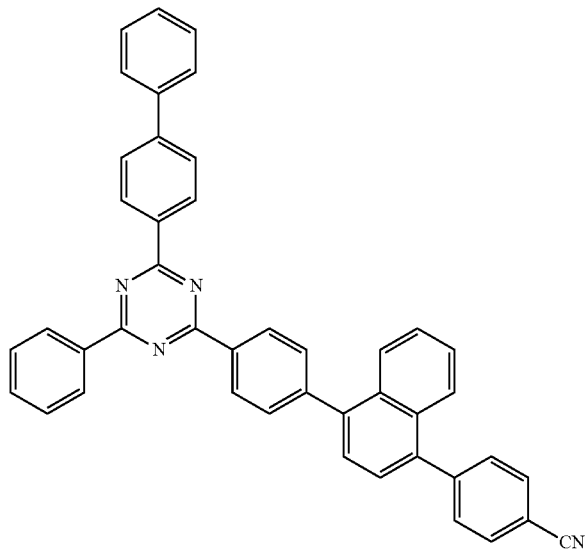
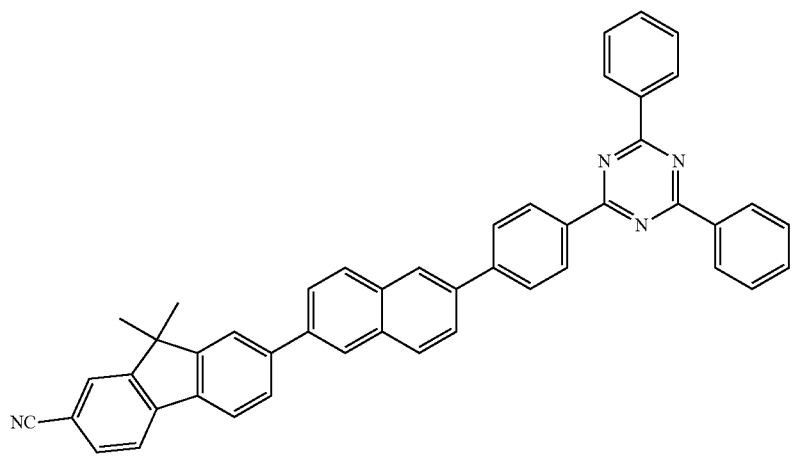
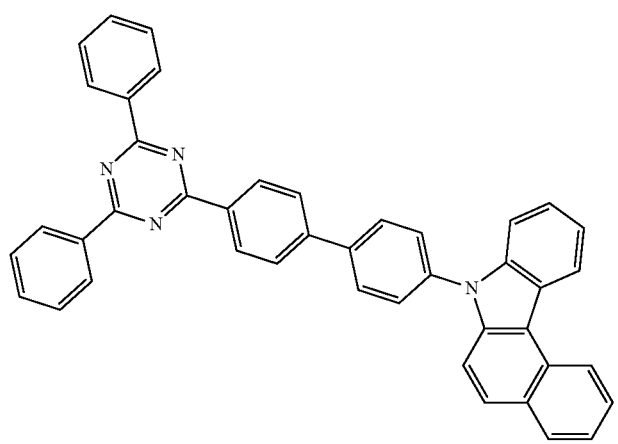

-continued
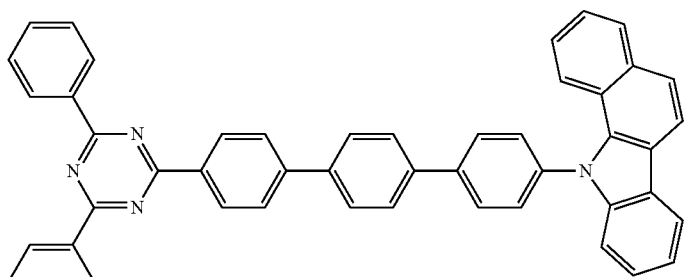
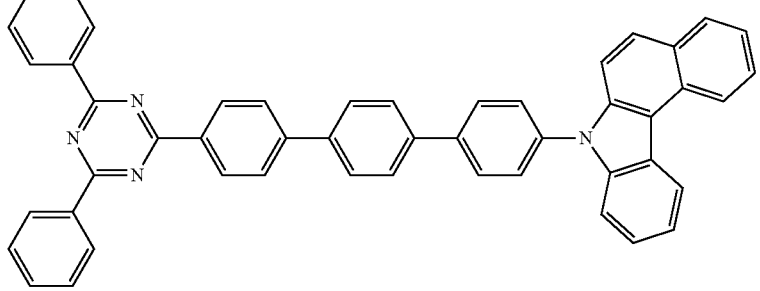
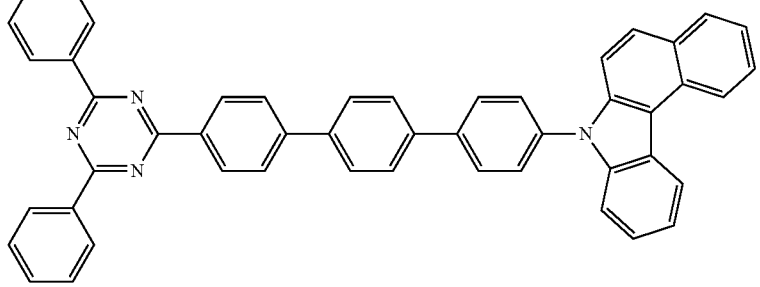
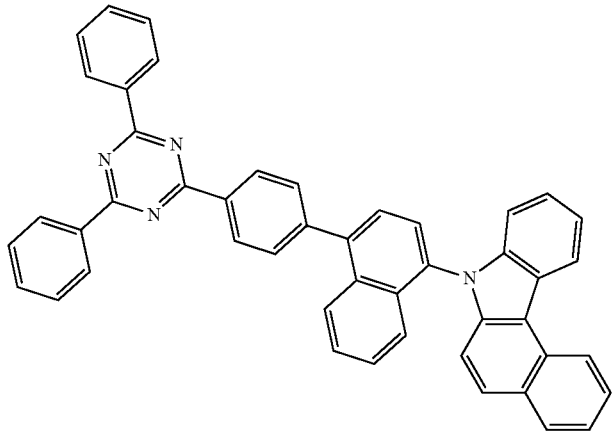
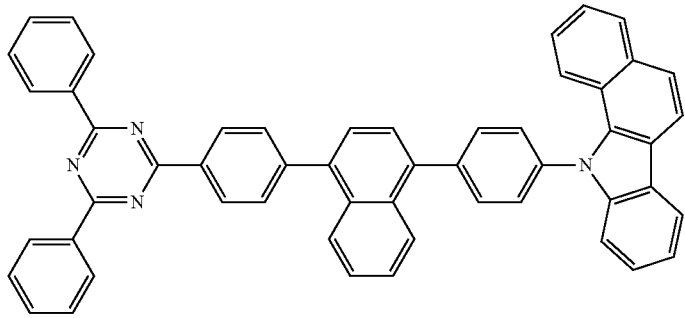

-continued

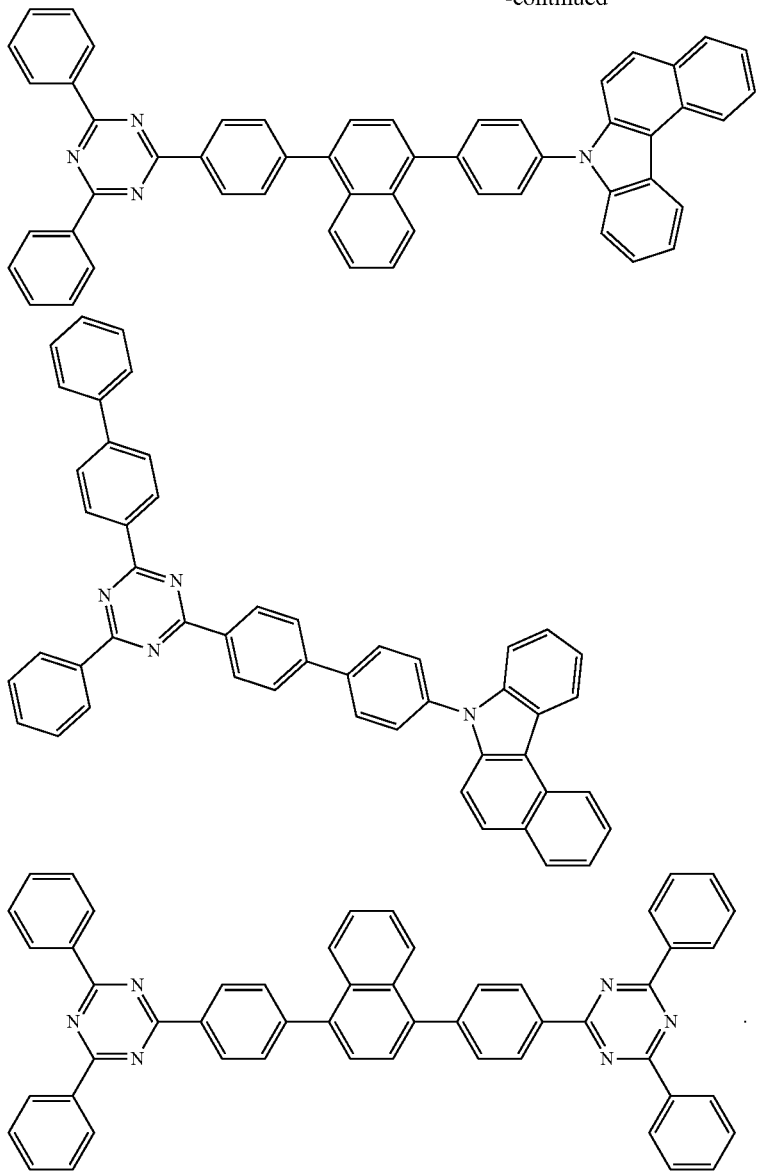

11. The organic light emitting device of claim 1, wherein the light emitting efficiency ($Eff_{0.1}$) measured at a current density of 0.1 mA/cm², and the light emitting efficiency ($Eff_{10}$) measured at a current density of 10 mA/cm² for the organic light emitting device satisfies the following Mathematical Formula 1:

$(Eff_{10}-Eff_{0.1})/Eff_{0.1} \leq 0.20$  [Mathematical Formula 1].

12. The organic light emitting device of claim 1, wherein the electron mobility of the power efficiency enhancement layer is larger than the electron mobility of the gradation enhancement layer.

* * * * *